United States Patent [19]
Lok et al.

[11] Patent Number: 5,959,075
[45] Date of Patent: Sep. 28, 1999

[54] TESTIS-SPECIFIC INSULIN HOMOLOG POLYPEPTIDES

[75] Inventors: Si Lok; Darrell C. Conklin, both of Seattle; Robyn L Adams, Bellevue; Anna C. Jelmberg, Issaquah; Catherine E. Lofton-Day, Brier; Stephen R. Jaspers, Edmonds, all of Wash.

[73] Assignee: ZymoGenetics, Inc., Seattle, Wash.

[21] Appl. No.: 08/905,267

[22] Filed: Aug. 1, 1997

Related U.S. Application Data

[60] Provisional application No. 60/023,213, Aug. 2, 1996, and provisional application No. 60/031,592, Nov. 21, 1996.

[51] Int. Cl.$^6$ ............................................. A61K 38/28
[52] U.S. Cl. ........................... 530/303; 514/2; 514/3
[58] Field of Search ............................ 530/303; 514/2, 514/3

[56] References Cited

FOREIGN PATENT DOCUMENTS

| 351 045 A2 | 1/1990 | European Pat. Off. . |
| 93/11247 | 6/1993 | WIPO . |
| 95/00645 | 1/1995 | WIPO . |
| 97/16549 | 5/1997 | WIPO . |

OTHER PUBLICATIONS

Bagnell et al., *Journal of Reproduction and Fertility Supplement* 48: 127–138, 1993.
Zhu et al., *Proc. Natl. Acad. Sci. U.S.A.* 94: 4704–4709, 1997.
Juang et al., *Animal Reproduction Science* 20: 21–29, 1989.
Pusch et al., *Endocrinology* 137: 3009–3013, 1996.
Gunnersen et al., *Molecular and Cellular Endocrinology* 110: 55–64, 1995.
Park et al., *Am. J. Obstet. Gynecol.* 158: 974–979, 1988.
Lessing et al., *Journal of Reproductive Medicine* 31: 304–309, 1986.
Juang et al., *Animal Reproductive Science* 22: 47–53, 1990.
Carrell et al., *Endocrine Research* 21: 697–707, 1995.
Lessing et al., *Fertility and Sterility* 44: 406–409, 1985.
Colon et al., *Fertility and Sterility* 46: 1133–1139, 1986.
Chassin et al., *Genomics* 29: 465–470, 1995.
TIGR Tentative human consensus, 1997.
Davis, PatentSequence, 1997.
Guellaen, INSERM, 1994.

*Primary Examiner*—David Saunders
*Assistant Examiner*—F. Pierre VanderVegt
*Attorney, Agent, or Firm*—Susan E. Lingenfelter; Deborah A. Sawislak

[57] ABSTRACT

The present invention provides testis-specific insulin homolog polypeptides and polynucleotides encoding the polypeptides, as well as related compositions and methods are disclosed. The polypeptides and polynucleotides may be used within methods for enhancing viability of cryopreserved sperm, for enhancing sperm motility, to enhance fertilization in methods of assisted reproduction, as contraceptives and other related uses.

8 Claims, 2 Drawing Sheets

FIGURE 1A

```
              +....110..+....120..+....130..+....140..+....150..+....160..+....170..+...180
IGF2_HUMAN    FPRYPVGKFFQYDTWKQSTQRLRRGLPALLRARRGHVLAKELEAFREAKRHRPLIALPTQDPAHGGAPPEMASNRK
INS_HUMAN     +....110..+....120..+....130..+....140..+....150..+....160..+....170..+...180
REL2_HUMAN    +....110..+....120..+....130..+....140..+....150..+....160..+....170..+...180
REL1_HUMAN    +....110..+....120..+....130..+....140..+....150..+....160..+....170..+...180
HSLILH        +....110..+....120..+....130..+....140..+....150..+....160..+....170..+...180
INSL4         +....110..+....120..+....130..+....140..+....150..+....160..+....170..+...180
zins2_rat     +....110..+....120..+....130..+....140..+....150..+....160..+....170..+...180
zins2_human   Y
```

FIGURE 1B

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 566 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..566

(xi) SEQUENCE DESCRIPTION: SEQ ID NO:1:

| | | |
|---|---|---|
| ATG AAG CAG CTG TGC TGT TCT TGT CTG TTG TGG CTT GGA CTC CTA CTG | | 48 |
| Met Lys Gln Leu Cys Cys Ser Cys Leu Leu Trp Leu Gly Leu Leu Leu | | |
| 1 5 10 15 | | |
| GCT CCT TTC TCC CAG GAA CAA GAA GAG GTC ACC AGC CCC ACG AAG TTG | | 96 |
| Ala Pro Phe Ser Gln Glu Gln Glu Glu Val Thr Ser Pro Thr Lys Leu | | |
| 20 25 30 | | |
| TGC GGC AGG GAC CTG TTG GTA GAA GTT ATA AAA CTC TGT GGC CAA AAT | | 144 |
| Cys Gly Arg Asp Leu Leu Val Glu Val Ile Lys Leu Cys Gly Gln Asn | | |
| 35 40 45 | | |
| GAC TGG AGC CGG TTC TCG ATG GAA GAG CAA AGT CCT ATG ACA GAG TTG | | 192 |
| Asp Trp Ser Arg Phe Ser Met Glu Glu Gln Ser Pro Met Thr Glu Leu | | |
| 50 55 60 | | |
| GTT CCC CAA TAT ACA CGG AAA GTC AAA ACC TTC AAC CCT CAC CGG TCC | | 240 |
| Val Pro Gln Tyr Thr Arg Lys Val Lys Thr Phe Asn Pro His Arg Ser | | |
| 65 70 75 80 | | |
| TCC TCC TCC TGG GGA AGA TTC ACA AAC CCA GGC GTC TCC CAG AAG AAA | | 288 |
| Ser Ser Ser Trp Gly Arg Phe Thr Asn Pro Gly Val Ser Gln Lys Lys | | |
| 85 90 95 | | |
| GCA ACA CAC ACT TGG GAA TCT CAG TCA CTG CCC AAC TAT CAG CTT AAA | | 336 |
| Ala Thr His Thr Trp Glu Ser Gln Ser Leu Pro Asn Tyr Gln Leu Lys | | |
| 100 105 110 | | |
| AAG GAG GAG CTG CTT CCG AAG ACA GGA GTG CAT TCA TAC CAC GGT GGC | | 384 |
| Lys Glu Glu Leu Leu Pro Lys Thr Gly Val His Ser Tyr His Gly Gly | | |
| 115 120 125 | | |
| AAG CCC TAT GTG AAG AGT GTA AAA TTT CAG AAG AAA AAC ACT GAC AAA | | 432 |
| Lys Pro Tyr Val Lys Ser Val Lys Phe Gln Lys Lys Asn Thr Asp Lys | | |
| 130 135 140 | | |
| ATG AGT ACC TTC AGC GGC TTA TTT TGG GGG AAC CAT CCC CAG AGG AAG | | 480 |
| Met Ser Thr Phe Ser Gly Leu Phe Trp Gly Asn His Pro Gln Arg Lys | | |
| 145 150 155 160 | | |
| CGC AGA GGT TTC GCA GAT AAA TGC TGT GCT ATA GGG TGC TCC AAA GAG | | 528 |
| Arg Arg Gly Phe Ala Asp Lys Cys Cys Ala Ile Gly Cys Ser Lys Glu | | |
| 165 170 175 | | |
| GAG CTG GCC GTC GCA TGC CTT CCG TTT GTT GAT TTT TA | | 566 |
| Glu Leu Ala Val Ala Cys Leu Pro Phe Val Asp Phe | | |
| 180 185 | | |

(2) INFORMATION FOR SEQ ID NO:2:

(i) SEQUENCE CHARACTERISTICS:
        (A) LENGTH: 188 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Gln Leu Cys Cys Ser Cys Leu Leu Trp Leu Gly Leu Leu Leu
1               5                   10                  15

Ala Pro Phe Ser Gln Glu Gln Glu Glu Val Thr Ser Pro Thr Lys Leu
                20                  25                  30

Cys Gly Arg Asp Leu Leu Val Glu Val Ile Lys Leu Cys Gly Gln Asn
            35                  40                  45

Asp Trp Ser Arg Phe Ser Met Glu Glu Gln Ser Pro Met Thr Glu Leu
        50                  55                  60

Val Pro Gln Tyr Thr Arg Lys Val Lys Thr Phe Asn Pro His Arg Ser
65                  70                  75                  80

Ser Ser Ser Trp Gly Arg Phe Thr Asn Pro Gly Val Ser Gln Lys Lys
                85                  90                  95

Ala Thr His Thr Trp Glu Ser Gln Ser Leu Pro Asn Tyr Gln Leu Lys
            100                 105                 110

```
Lys Glu Glu Leu Leu Pro Lys Thr Gly Val His Ser Tyr His Gly Gly
            115                 120                 125

Lys Pro Tyr Val Lys Ser Val Lys Phe Gln Lys Lys Asn Thr Asp Lys
        130                 135                 140

Met Ser Thr Phe Ser Gly Leu Phe Trp Gly Asn His Pro Gln Arg Lys
145                 150                 155                 160

Arg Arg Gly Phe Ala Asp Lys Cys Cys Ala Ile Gly Cys Ser Lys Glu
                165                 170                 175

Glu Leu Ala Val Ala Cys Leu Pro Phe Val Asp Phe
            180                 185
```

(2) INFORMATION FOR SEQ ID NO:3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (vii) IMMEDIATE SOURCE:
        (B) CLONE: ZC6091

(xi) SEQUENCE DESCRIPTION: SEQ ID NO:3:

```
GAGCACAGAA TTCACTACTC GAGGCGGCCG CTTTTTTTTT TTTTTTTTT        49
```

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (vii) IMMEDIATE SOURCE:
        (B) CLONE: ZC10008

(xi) SEQUENCE DESCRIPTION: SEQ ID NO:4:

```
CAGGTCGACA CCATGCCGCG GCTCCTCCGC TT        32
```

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC10491

(xi) SEQUENCE DESCRIPTION: SEQ ID NO:5:

```
GAGTCTAGAT TATGTCACTC ATACAGGAAA GCTC        34
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC10684

(xi) SEQUENCE DESCRIPTION: SEQ ID NO:6:

```
TCCTCCGCTT GTCCCTGCTG TGG        23
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (vii) IMMEDIATE SOURCE:
        (B) CLONE: ZC10685

(xi) SEQUENCE DESCRIPTION: SEQ ID NO:7:

```
CTCCTCGAAA CGGAACTGGC TCC                                             23
```

(2) INFORMATION FOR SEQ ID NO:8:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (xi) SEQUENCE DESCRIPTION: SEQ ID NO:8:

```
GTCGACACCA TGCCGCGGCT CCTCCGCTTG TCCCTGCTGT GGCTTGGACT CCTGCTGGTT     60
CGGTTTTCTC GTGAACTGAG CGACATCAGC AGTGCCAGGA AGCTGTGCGG CAGGTACTTG    120
GTGAAAGAAA TAGAAAAACT CTGCGGCCAT GCCAACTGGA GCCAGTTCCG TTTCGAGGAG    180
GAAACCCCTT TCTCACGGTT GATTGCACAG GCCTCGGAGA AGGTCGAAGC CTACAGCCCA    240
TACCAGTTCG AAAGCCCGCA AACCGCTTCC CCGGCCCGGG GAAGAGGCAC AAACCCAGTG    300
TCTACTTCTT GGGAAGAAGC AGTAAACAGT TGGGAAATGC AGTCACTACC TGAGTATAAG    360
GATAAAAAGG GATATTCACC CCTTGGTCTG CTGGAGTTTG CTGGAGGCCC ACTCCAGATG    420
CTGTTTGCCT GGGTATCACC AGCAGAGGCT GCAGAACAGC AAAGATTGCT GCCTGTTCCT    480
TCCTCTGGAA GCTTCATCCC AGAGGGGCAC CCACTAGATG CCAGCCAGAG CTTTCCTGTA    540
TGAGTGACAT AAGGATTCAA CTTCAACAGA ATTC                                574
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (vii) IMMEDIATE SOURCE:
        (B) CLONE: ZC10491

(xi) SEQUENCE DESCRIPTION: SEQ ID NO:9:

```
CGACCGCCAT TGCACAACGC GGAGGA                                          26
```

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (vii) IMMEDIATE SOURCE:
        (B) CLONE: ZC10537

(xi) SEQUENCE DESCRIPTION: SEQ ID NO:10:

```
ATAGGAGGAA AGGTTGTTGT TGACAAAGAA ACTTG                                35
```

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (vii) IMMEDIATE SOURCE:
        (B) CLONE: ZC10538

(xi) SEQUENCE DESCRIPTION: SEQ ID NO:11:

GACGAATTCT GTTGAAGTTG AATCCTTATG TCAC                                           34

(2) INFORMATION FOR SEQ ID NO:12:

(i) SEQUENCE CHARACTERISTICS:
        (A) LENGTH: 703 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 17..658

(xi) SEQUENCE DESCRIPTION: SEQ ID NO:12:

```
GCCTGGGGTC ACAGGG ATG CCG CGG CTC CTC CGC TTG TCC CTG CTG TGG          49
               Met Pro Arg Leu Leu Arg Leu Ser Leu Leu Trp
                1               5                  10

CTT GGA CTC CTG CTG GTT CGG TTT TCT CGT GAA CTG AGC GAC ATC AGC        97
Leu Gly Leu Leu Leu Val Arg Phe Ser Arg Glu Leu Ser Asp Ile Ser
             15                  20                  25

AGT GCC AGG AAG CTG TGC GGC AGG TAC TTG GTG AAA GAA ATA GAA AAA       145
Ser Ala Arg Lys Leu Cys Gly Arg Tyr Leu Val Lys Glu Ile Glu Lys
         30                  35                  40

CTC TGC GGC CAT GCC AAC TGG AGC CAG TTC CGT TTC GAG GAG GAA ACC       193
Leu Cys Gly His Ala Asn Trp Ser Gln Phe Arg Phe Glu Glu Glu Thr
     45                  50                  55

CCT TTC TCA CGG TTG ATT GCA CAG GCC TCG GAG AAG GTC GAA GCC TAC       241
Pro Phe Ser Arg Leu Ile Ala Gln Ala Ser Glu Lys Val Glu Ala Tyr
 60                  65                  70                  75

AGC CCA TAC CAG TTC GAA AGC CCG CAA ACC GCT TCC CCG GCC CGG GGA       289
Ser Pro Tyr Gln Phe Glu Ser Pro Gln Thr Ala Ser Pro Ala Arg Gly
             80                  85                  90

AGA GGC ACA AAC CCA GTG TCT ACT TCT TGG GAA GAA GCA GTA AAC AGT       337
Arg Gly Thr Asn Pro Val Ser Thr Ser Trp Glu Glu Ala Val Asn Ser
         95                 100                 105

TGG GAA ATG CAG TCA CTA CCT GAG TAT AAG GAT AAA AAG GGA TAT TCA       385
Trp Glu Met Gln Ser Leu Pro Glu Tyr Lys Asp Lys Lys Gly Tyr Ser
    110                 115                 120

CCC CTT GGT AAG ACA AGA GAA TTT TCT TCA TCA CAT AAT ATC AAT GTA       433
Pro Leu Gly Lys Thr Arg Glu Phe Ser Ser Ser His Asn Ile Asn Val
125                 130                 135

TAT ATT CAT GAG AAT GCA AAA TTT CAG AAG AAA CGT AGA AAC AAA ATT       481
Tyr Ile His Glu Asn Ala Lys Phe Gln Lys Lys Arg Arg Asn Lys Ile
140                 145                 150                 155

AAA ACC TTA AGC AAT TTG TTT TGG GGG CAT CAT CCC CAA AGA AAA CGC       529
Lys Thr Leu Ser Asn Leu Phe Trp Gly His His Pro Gln Arg Lys Arg
                160                 165                 170

AGA GGA TAT TCA GAA AAG TGT TGT CTT ACA GGA TGT ACA AAA GAA GAA       577
Arg Gly Tyr Ser Glu Lys Cys Cys Leu Thr Gly Cys Thr Lys Glu Glu
            175                 180                 185
```

```
CTT AGC ATT GCA TGT CTT CCA TAT ATT GAT TTT AAA AGG CTA AAG GAA      625
Leu Ser Ile Ala Cys Leu Pro Tyr Ile Asp Phe Lys Arg Leu Lys Glu
        190                 195                 200

AAA AGA TCA TCA CTT GTA ACT AAG ATA TAC TAACCATCTT AGAATTTTTT         675
Lys Arg Ser Ser Leu Val Thr Lys Ile Tyr
        205                 210

CTAACCTAAT AAAAGCTTAA TACATTTA                                        703
```

(2) INFORMATION FOR SEQ ID NO:13:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:13:

```
Met Pro Arg Leu Leu Arg Leu Ser Leu Leu Trp Leu Gly Leu Leu Leu
 1               5                  10                  15

Val Arg Phe Ser Arg Glu Leu Ser Asp Ile Ser Ser Ala Arg Lys Leu
                20                  25                  30

Cys Gly Arg Tyr Leu Val Lys Glu Ile Glu Lys Leu Cys Gly His Ala
        35                  40                  45

Asn Trp Ser Gln Phe Arg Phe Glu Glu Glu Thr Pro Phe Ser Arg Leu
    50                  55                  60

Ile Ala Gln Ala Ser Glu Lys Val Glu Ala Tyr Ser Pro Tyr Gln Phe
65                  70                  75                  80

Glu Ser Pro Gln Thr Ala Ser Pro Ala Arg Gly Arg Gly Thr Asn Pro
                85                  90                  95

Val Ser Thr Ser Trp Glu Glu Ala Val Asn Ser Trp Glu Met Gln Ser
                100                 105                 110

Leu Pro Glu Tyr Lys Asp Lys Lys Gly Tyr Ser Pro Leu Gly Lys Thr
            115                 120                 125

Arg Glu Phe Ser Ser Ser His Asn Ile Asn Val Tyr Ile His Glu Asn
        130                 135                 140

Ala Lys Phe Gln Lys Lys Arg Arg Asn Lys Ile Lys Thr Leu Ser Asn
145                 150                 155                 160

Leu Phe Trp Gly His His Pro Gln Arg Lys Arg Arg Gly Tyr Ser Glu
                165                 170                 175

Lys Cys Cys Leu Thr Gly Cys Thr Lys Glu Glu Leu Ser Ile Ala Cys
                180                 185                 190

Leu Pro Tyr Ile Asp Phe Lys Arg Leu Lys Glu Lys Arg Ser Ser Leu
            195                 200                 205

Val Thr Lys Ile Tyr
210
```

TESTIS-SPECIFIC INSULIN HOMOLOG POLYPEPTIDES

REFERENCE TO RELATED APPLICATIONS

This application is related to Provisional application Ser. Nos. 60/023,213, filed on Aug. 2, 1996; and 60/031,592, filed on Nov. 21, 1996. Under 35 U.S.C. § 119(e)(1), this application claims benefit of said Provisional Applications.

BACKGROUND OF THE INVENTION

Proliferation and differentiation of cells within multicellular organisms is controlled by hormones and polypeptide growth factors. These diffusable molecules allow cells to communicate with each other and act in concert to form organs, and to repair and regenerate damaged tissue. Examples of hormones and growth factors include the steroid hormones (e.g., estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO), insulin and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as certain transcription factors.

Insulin belongs to a group of protein/polypeptide hormones. Insulin increases the rate of synthesis of glycogen, fatty acids, and proteins and stimulates glycolysis. It also promotes the transport of glucose, some other sugars, and amino acids into muscle and fat cells. The mature form of insulin consists of a 30 amino acid residue B chain, that is at the N-terminus of the propeptide form, and a 21 amino acid residue A chain, that is C-terminal. Proinsulin also contains a connecting peptide, C-peptide, between the B chain and A chain that is cleaved out to form mature insulin. The B chain and A chain are covalently joined by two disulfide bonds. The B-chain, C-peptide, A-chain motif is found in several other proteins including, relaxin (U.S. Pat. No. 4,835,251, incorporated herein by reference), insulin-like growth factors (IGF) I and II (Bang and Hall, In "Insulin-like Growth Factors", P. N. Schofield (eds.), 151–177, Oxford Univ. Press, Oxford; incorporated herein by reference), Leydig factor (Bullesbach et al., *J. Biol. Chem.* 270: 16011–16015, 1995; incorporated herein by reference), and early placenta insulin-like factor (EPIL; Chassin et al., *Genomics* 29: 465–470, 1995, incorporated herein by reference). Unlike the other members of the insulin superfamily, IGF I and IGF II have D and E domains that are cleaved post-translationally. Cysteines that are involved in disulfide bonds are conserved in all the members of the family and play a role in the tertiary structure of the molecules.

Spermatogenesis is the process by which a germ cell proceeds through multiple stages of differentiation, and culminates in the formation of a terminally differentiated cell with a unique function. Hematopoiesis can be used as a paradigm for understanding spermatogenesis, and while there are striking parallels between what is known about hematopoiesis and spermatogenesis, the maturation of spermatogonia (germ cells) is less clearly understood than the maturation of hematopoietic stem cells. Particularly deficient is an understanding of factors that regulate the maturation process in spermatogenesis. Recent evidence suggests that some cytokines involved in the progression of stem cells of the hematopoietic lineage to fully differentiated cells are also involved in sperm cell maturation. In a fashion similar to cytokine action in hematopoiesis, these cytokines are thought to act at specific stages in the germ cell's maturation. For example, stem cell factor (also known as Steel factor and c-kit ligand) mRNA is expressed in spermatogonia (Manova et al., *Development* 110: 1057–1066, 1990), and administration of a monoclonal antibody to stem cell factor to adult or prepubertal mice causes depletion of differentiating spermatogonia but has no effect on the non-differentiating spermatogonia, or spermatocytes (Yoshinaga et al., *Development* 113: 689–699, 1991). Other cytokines that have been associated with spermatogenesis include IL-1, IL-6 and β-TGF (Sharp, Regulation of Spermatogenesis, in Knobil and Neil (ed.), *Physiol. Reproduction,* (2nd ed.), Raven, N.Y., 1994).

Because growth factors have had an enormous impact on our understanding of and ability to treat metabolic and cellular disorders, discovery of new factors is important. A new growth factor found in testis is particularly important for elucidating the spermatogenic process and potentially affecting the outcome of that process.

SUMMARY OF THE INVENTION

The present invention provides an isolated testis-specific insulin homolog polypeptide selected from the group consisting of: (a) polypeptides comprising a sequence of amino acids encoded by the nucleotide sequence as shown in SEQ ID NO: 1; (b) species homologs of (a); (c) allelic variants of (a) and (b); and (d) testis-specific insulin homolog polypeptides which are at least 85% identical to (a), (b) or (c).

In another aspect, the present provides an isolated polynucleotide molecule selected from the group consisting of: (a) DNA molecules encoding a testis-specific insulin homolog polypeptide and comprising a nucleotide sequence as shown in SEQ ID NO: 1 from nucleotide 1 to nucleotide 564; (b) species homologs of (a); (c) allelic variants of (a) or (b); (d) DNA molecules encoding a testis-specific insulin homolog polypeptide which are least 85% identical in nucleotide sequence to (a), (b), or (c); and (e) degenerate nucleotide sequences encoding a testis-specific insulin homolog polypeptide.

In another aspect, the present invention provides an expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) species homologs of (a); (c) allelic variants of (a) or (b); (d) DNA molecules encoding a testis-specific insulin homolog polypeptide and which are least 85% identical in nucleotide sequence to (a), (b), or (c); and a transcriptional terminator.

In another aspect, the present invention provides a cultured cell into which has been introduced an expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) species homologs of (a); (c) allelic variants of (a) or (b); (d) DNA molecules encoding a testis-specific insulin homolog polypeptide which are least 85% identical in nucleotide sequence to (a), (b), or (c); and a transcriptional terminator, and wherein the cell expresses a testis-specific insulin homolog polypeptide encoded by the DNA segment.

In another aspect, the present invention provides a method for producing a testis-specific insulin homolog polypeptide comprising culturing a cell into which has been introduced a first expression vector comprising the following operably linked elements: a transcriptional promoter; a DNA segment selected from the group consisting of: (a) DNA molecules encoding a testis-specific insulin homolog polypeptide and comprising a nucleotide sequence as shown in SEQ ID NO: 1 from nucleotide 1 to nucleotide 564; (b) species homologs of (a); (c) allelic variants of (a) or (b); (d) DNA molecules encoding a testis-specific insulin homolog polypeptide which are least 85% identical in nucleotide sequence to (a), (b), or (c); and a transcriptional terminator, whereby the cell expresses a testis-specific insulin homolog polypeptide encoded by the DNA segment, and recovering the testis-specific insulin homolog. Within one embodiment is provided a method for producing a Zins2 testis-specific insulin homolog polypeptide wherein the cell further comprises a second expression vector comprising the following operably linked elements: a transcriptional promoter; a DNA sequence encoding a prohormone convertase; and a transcriptional terminator. Within a related embodiment the prohormone convertase is selected from the group consisting of prohormone convertase 2, prohormone convertase 3, prohormone convertase 4 and furin.

Within another aspect, the invention provides an isolated, mature rat Zins2 testis-specific insulin homolog protein having: a B chain comprising amino acid residue 22 to amino acid residue 52 of SEQ ID NO:2; an A chain comprising amino acid residue 162 to amino acid residue 188 of SEQ ID NO:2; wherein the B chain and A chain are joined by inter- and intra-chain disulfide bonds. Within a related embodiment is provided an isolated, mature rat Zins2 testis-specific insulin homolog protein having: a B chain having the amino acid sequence from amino acid residue 23 to amino acid residue 51 of SEQ ID NO:2; an A chain having the amino acid sequence from amino acid residue 163 to amino acid residue 188 of SEQ ID NO:2, wherein the B chain and A chain are joined by inter- and intra-chain disulfide bonds.

The invention also provides an isolated, mature human Zins2 testis-specific insulin homolog protein having: a B chain comprising amino acid residue 20 to amino acid residue 54 of SEQ ID NO:13; an A chain comprising amino acid residue 172 to amino acid residue 213 of SEQ ID NO:13; wherein the B chain and A chain are joined by inter- and intra-chain disulfide bonds. Within a related embodiment is provided an isolated, mature human Zins2 testis-specific insulin homolog protein having: a B chain having the amino acid sequence from amino acid residue 21 to amino acid residue 53 of SEQ ID NO:13; an A chain having the amino acid sequence from amino acid residue 173 to amino acid residue 198 of SEQ ID NO:13, wherein the B chain and A chain are joined by inter- and intra-chain disulfide bonds.

Within another aspect, the invention provides a post-translationally modified Zins2 testis-specific insulin homolog polypeptide or polypeptide fragment having the amino acid sequence from amino acid residue 53 to amino acid residue 162 of SEQ ID NO:2; the amino acid sequence from amino acid residue 55 to amino acid residue 172 of SEQ ID NO:13 or the amino acid sequence from amino acid residue 201 to amino acid residue 213 of SEQ ID NO:13.

The invention also provides a pharmaceutical composition comprising an isolated testis-specific insulin homolog polypeptide as described above in combination with a pharmaceutically acceptable vehicle.

Also provided by the invention is an antibody that specifically binds to an epitope of an isolated testis-specific insulin homolog polypeptide as described above.

The invention further provides a binding protein that specifically binds to an epitope of an isolated testis-specific insulin homolog polypeptide as described above.

The invention additionally provides a binding protein that specifically binds to an epitope of a polypeptide selected from the group consisting of: (a) polypeptides comprising a sequence of amino acids encoded by the nucleotide sequence as shown in SEQ ID NO:12; (b) species homologs of (a); (c) allelic variants of (a) and (b); and (d) testis-specific insulin homolog polypeptides which are at least 85% identical to (a), (b) or (c).

Within another aspect, the invention provides a method of enhancing viability of cryopreserved sperm for use in fertilization of an egg, wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is added to sperm, an egg, an egg-sperm mixture, prior to fertilization.

Within another aspect, the invention provides a method of enhancing sperm motility wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is added to sperm, an egg, an egg-sperm mixture, prior to fertilization. Within a related embodiment is provided a method of enhancing sperm motility wherein the Zins2 testis-specific insulin homolog is added to sperm following cryopreservation.

Within another aspect, the invention provides a method of enhancing an egg-sperm interaction wherein a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is added to sperm, an egg, an egg-sperm mixture prior to fertilization.

Within anther aspect, the invention provides a method of enhancing fertilization during assisted reproduction wherein a Zins2 testis-specific insulin homolog polypeptide selected from the group consisting of:

(a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is combined with sperm, an egg, an egg-sperm mixture prior to fertilization of the egg. Within one embodiment is provided a method of enhancing fertilization wherein the assisted reproduction is artificial insemination. Within a related embodiment is provided a method of enhancing fertilization wherein the assisted reproduction is in vitro fertilization.

Also provided by the invention is a method of contraception wherein an antagonist of a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is administered to a recipient to prevent fertilization of an egg. Within a related embodiment is provided a method of contraception according wherein the antagonist is an anti-Zins2 binding protein.

The invention further provides a method of immunocontraception wherein a vaccine containing a Zins2 testis-specific insulin homolog polypeptide selected from the group consisting of: (a) polypeptides comprising a sequence of amino acids encoded by the nucleotide sequence as shown in SEQ ID NO: 1 or SEQ ID NO:12; (b) species homologs of (a); (c) allelic variants of (a) and (b); and (d) Zins2 testis-specific insulin homolog polypeptides which are at least 85% identical to (a), (b) or (c) is administered to a recipient to prevent fertilization of an egg.

BRIEF DESCRIPTION OF THE DRAWINGS

FIGS. 1A and 1B show a multiple alignment of human IGF I, human IGF II, human insulin, human relaxin 2, human relaxin 1, human Leydig factor (HSLILH), human INSL4 (early placenta insulin-like factor or EPIL), rat and human Zins2.

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The present invention is based in part upon the discovery of a novel DNA sequence that encodes a polypeptide with homology to the insulin family (i.e., insulin, relaxin, Leydig factor, INSL-4, IGF I and IGF II). The DNA sequence was designated Zins2. Analysis of the tissue distribution of the mRNA corresponding to this novel DNA showed that expression was restricted to the testis. In situ hybridization analysis demonstrated that mRNA is localized in the seminiferous tubules and epididymus, suggesting a role as a growth or differentiation factor for testis-specific cell types and involvement in sperm activation.

Spermatogenesis is a sequential process and takes place in the seminiferous tubules, where germ cells ultimately mature into spermatozoa, herein referred to as sperm. Testis-specific factors that influence the maturation process may come directly from the Sertoli cells that are in contact with spermatogenic cells, or may be paracrine or endocrine factors. Many of the molecules produced outside the seminiferous tubules are transported into the sperm cell microenvironment by transport and binding proteins that are expressed by the Sertoli cells within the seminiferous tubules.

Paracrine factors that cross the cellular barrier and enter the sperm cell microenvironment include molecules secreted from Leydig cells. Leydig cells are located in the interstitial space found between the seminiferous tubules, and produce several factors believed to play an important role in spermatogenic cell maturation process, such as testosterone, Leydig factor, IGF-1, inhibin and activin. The expression of these, and other factors, may be specific to a defined stage in the spermatogenic cycle. The sperm is then transported to the epididymus, where sperm motility and fertilization capacity are increased. The sperm is stored in the tail of the epididymus until released.

Before reaching the oocyte or egg and initiating an egg-sperm interaction, the sperm must be activated. The sperm undergo a gradual capacitation, lasting up to 3 or 4 hours in vitro, during which the plasma membrane of the sperm head and the outer acrosomal membrane fuse to form vesicles that facilitate the release of acrosomal enzymes. The acrosomal membrane surrounds the acrosome or acrosomal cap which is located at the anterior end of the nucleus in the sperm head.

In order for the sperm to interact with the egg the sperm must penetrate the oocyte. To enable this process the sperm must undergo acrosomal exocytosis, also known as the acrosomal reaction, and release the acrosomal enzymes in the vicinity of the oocyte. These enzymes enable the sperm to penetrate the various oocyte layers, (the cumulus oophorus, the corona radiata and the zona pellucida) and initiate an interaction with the egg. The released acrosomal enzymes include hyaluronidase and proacrosin, in addition to other enzymes such as proteases. During the acrosomal reaction, proacrosin is converted to acrosin, the active form of the enzyme, which is required for and must occur before binding and penetration of the zona pellucida is possible. A combination of the acrosomal lytic enzymes and sperm tail movements provide the sperm with the ability to penetrate the oocyte layers. Numerous sperm must reach the egg and release their acrosomal enzymes before the egg can finally be fertilized. Only one sperm will successfully bind to and penetrate the egg, after which the zona hardens so that no other sperm can penetrate and fertilization of the egg occurs (Zaneveld, in Male Infertility Chapter 11, Comhaire (Ed.), Chapman & Hall, London 1996). Insulin homologs have been associated with sperm activation and egg-sperm interaction. For instance, capacitated sperm incubated with relaxin showed an increased percentage of progressively motile sperm, increased zona penetration rates, and increased percentage of viable acrosome-reacted sperm (Carrell et al., *Endocr. Res.* 21: 697–707, 1995). Homology of the Zins2 proteins with relaxin and localization of Zins2 to the testis suggests that the Zins2 proteins described herein play a role in these and other reproductive processes.

Analysis of a rat cDNA encoding a testis-specific insulin homolog (SEQ ID NO: 1) revealed an opening reading frame encoding 188 amino acids (SEQ ID NO: 2), comprising a putative signal sequence and a mature polypeptide. The analysis of a representative human cDNA sequence encoding a testis-specific insulin homolog polypeptide revealed a similar homology, with an open reading frame of 213 amino acids as shown in SEQ ID NO: 13.

Figure 1A:
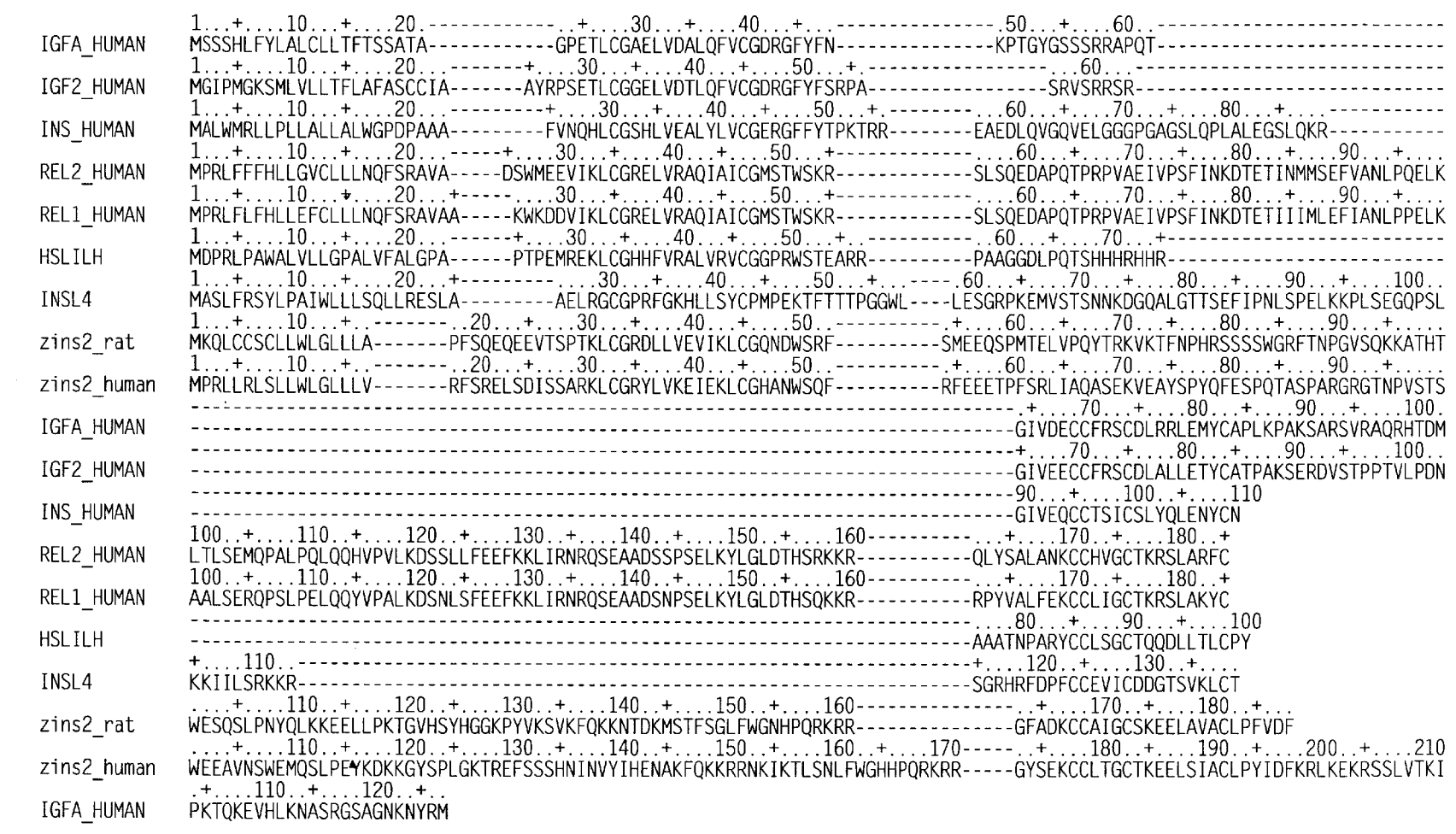

The mature polypeptide has homology with insulin, relaxin 1 and 2, INSL-4 and Leydig factor, respectively, as shown in FIGS. 1A and 1B. Within this family, the cysteine motif is highly conserved in the B and A chains, where the B chain motif can be represented as LCGX{10}C, where X{ } is the number of any amino acid residues except cysteine. The A chain motif is CCX{3}CX{8}C, where X{ } is the number of any amino acid residues, except cysteine.

Isolation of a rat cDNA sequence encoding testis-specific insulin homolog revealed that the predicted amino acid sequence contained the B chain-C peptide-A chain motif found in the relaxins and insulin. Preprorelaxin and preproinsulin both have a signal sequence, followed by the B chain, C peptide, and A chain. The mature molecule of both relaxin and insulin has the signal peptide and C peptide removed, with the B and A chains joined by both inter- and intra-chain disulfide bonds (James et al., *Nature* 267: 544–546, 1977). Isolation of a human clone and subsequent sequence analysis indicates that the human sequence (as shown in SEQ ID NO: 13) is structurally equivalent to other members of the family.

Processing of the mature protein molecule involves cleavage at the C-terminus of the signal peptide, and, based on predicted structural homology with other mature members of the insulin family, a cleavage at the C-terminus of the B chain and at the N-terminus of the A chain, resulting in removal of the C-peptide. Alignment of the rat testis-specific insulin homolog of the present invention with other known members of the insulin family (as shown in the FIGS. 1A and 1B) suggests a signal peptide cleavage site in the region of amino acid residue 22 (Glu) to amino acid residue 23 (Gln) of SEQ ID NO: 2. Cleavage at the C-terminus of the B chain is predicted to be at the C-terminal of amino acid residue 52 (Arg) followed by cleavage of the Arg residue by carboxypeptidase to leave amino acid residue 51 (Phe) as the C-terminal amino acid residue. Cleavage sites resulting in the N-terminus of the A chain are suggested in the region of amino acid residue 161 (Arg) to 163 (Gly). Cleavage is predicted to be after the C-terminus of amino acid residue 162 (Arg) leaving amino acid residue 163 (Gly) as the N-terminal amino acid residue of the A chain. The C-terminal amino acid is residue 188 (Phe). The cleavage site at the junction of the C-peptide and A chain is highly conserved, occurring after Arg-X-X-Arg (wherein X is any amino acid residue), Arg-Arg or Lys-Arg; however, the cleavage sites at the junction of the signal sequence and B chain, and at the junction of the B chain and C-peptide, do not maintain a similarly high degree of conservation within the insulin family.

Alignment of a representative human testis-specific insulin homolog polypeptide suggests signal peptide cleavage in the region of amino acid residue 20 (Ser) to residue 21 (Arg) of SEQ ID NO: 13. Cleavage at the C-terminus of the B chain is predicted to be C-terminal of amino acid residue 54 (Arg), followed by cleavage of the Arg residue by a carboxypeptidase, to leave amino acid residue 53 (Phe) as the C-terminal amino acid residue of the B chain. Cleavage sites resulting in the N-terminus of the A chain are suggested in the region of amino acid residue 171 (Arg) to 173 (Gly). Cleavage is predicted to be at the C-terminus of amino acid residue 172 (Arg) leaving amino acid residue 173 (Gly) as the N-terminal amino acid residue of the A chain.

There are several potential cleavage sites in the C-terminal portion of the predicted human Zins2 A chain sequence, for example C-terminal of the Arg at amino acid residue 200 or C-terminal of the Arg at amino acid residue 205. It is not obvious based on the amino acid sequence of the human Zins2 testis-specific insulin homolog (SEQ ID NO:13) alone, or in comparison with other insulin homologs (FIGS. 1A and 1B), which site is the A chain C-terminal cleavage site, or if there would be cleavage at all. IGF-1 has a furin cleavage site and multiple potential monobasic cleavage sites and consensus furin sites in the C-terminal of the A chain, while insulin and relaxin do not. A determination of which of the two possible sites is the actual cleavage site is not possible based on the human Zins2 sequence alone. Knowledge of the amino acid sequence of the rat Zins2 homolog (SEQ ID NO:2) enables a reasonable prediction of the C-terminal cleavage site for the human A chain. Human Zins2 has two potential cleavage sites wherein rat Zins2 does not. There is a cleavage site in the human sequence C-terminal of amino acid residue 200 (Arg). Cleavage at this site, followed by cleavage of the Arg (amino acid residue 200) and Lys (amino acid residue 199) residues by a carboxypeptidase, leaves amino acid residue 198 (Phe) as the C-terminal amino acid residue of the human A chain which corresponds to the rat sequence as disclosed in SEQ ID NO:2. It is therefore predicted, based on the rat Zins2 homolog, that C-terminal cleavage site of the human Zins2 A chain would be C-terminal of amino acid residue 200 (Arg) of SEQ ID NO:13.

Based on the predicted sites, the amino acid sequence of mature human Zins2 testis-specific insulin homolog include, a B chain having the sequence of SEQ ID NO:13 from amino acid residue 21 (Arg) to amino acid residue 53 (Phe), and an A chain having the sequence of SEQ ID NO:13 from amino acid residue 173 (Gly) to amino acid residue 198 (Phe). The amino acid sequence of the mature rat Zins2 testis-specific insulin homolog include, a B chain having the sequence of SEQ ID NO:2 from amino acid residue 23 (Gln) to amino acid residue 51 (Ser), and an A chain having the sequence of SEQ ID NO:2 from amino acid residue 163 (Gly) to amino acid residue 188 (Phe). The B and A chains are joined by inter- and intra-chain disulfide bonds.

The enzymology of proinsulin conversion suggests that prohormone convertase 3 (PC3) or other homolog-monobasic capable convertases, cleave primarily at the B chain-C-peptide junction, and that prohormone convertase 2 (PC2) or similar convertases cleave preferentially at the C-peptide-A-chain junction and favor proinsulin already processed by PC3 over intact prohormone. In human and rat proinsulin, dibasic residues link the B chain and C-peptide and the C-peptide and A chain. In addition, a basic residue 4 residues N-terminal to the cleavage site (a "P4 basic residue") may be present at one or both junctions, and may influence the ability of furin, or similar convertases of the furin family such as prohormone convertase 4 (PC4) and PACE4, to cleave at the junction sites. In a study reported by Vollenweider et al. (*Diabetes* 44: 1075–80, 1995), cotransfection of COS cells with PC3 and either human proinsulin, rat proinsulin II or mutant human proinsulin Arg$^{62}$ showed that PC3 cleaved both proinsulin junctions, regardless of the presence or absence of a P4 basic residue.

Within the relaxin proteins there is a highly conserved region in the B chain of Cys-Gly-Arg and Cys-Gly at amino acid residues 35 to 37 and amino acid residues 47 to 48, respectively, that is also found in the rat testis-specific insulin homolog protein of the present invention at amino acid residues 33 to 35 and amino acid residues 45 to 46 of SEQ ID NO: 2, respectively. The equivalent region in the human sequence shown in SEQ ID NO: 13 is amino acid residues 33–35 and 45–46, respectively and is shown in the FIGS. 1A and 1B. There is evidence that residues 35–41 (CGRELVR), as found in the relaxins (and shown in the FIGS. 1A and 1B), are important for binding the relaxin receptor (Bullesbach et al., *J. Biol. Chem.* 267: 22957–22960, 1992). The Zins2 testis-specific insulin homologs are missing one of the critical arginine residues, in the rat Zins2 sequence, the second arginine is replaced by valine (amino acid residue 39 of SEQ ID NO:2) and in the human Zins2 sequence, arginine is replaced by lysine (amino acid residue 39 of SEQ ID NO:13). This substitution does not rule out the possibility of cross-reactivity by the relaxins with Zins2, but it is unlikely that Zins2 would be cross-reactive with the relaxins.

Also provided by the present invention are post-translationally modified polypeptides or polypeptide fragments having the amino acid sequence from amino acid residue 53 to amino acid residue 162 of SEQ ID NO:2; the amino acid sequence from amino acid residue 55 to amino acid residue 172 of SEQ ID NO:13 or the amino acid sequence from amino acid residue 201 to amino acid residue 213 of SEQ ID NO:13. Examples of post translational modifications include proteolytic cleavage, glycosylation, disulfide bonding and hydroxylation. The C peptide from insulin, when administered to diabetic rats, decreased or prevented diabetes-induced damage to neurons or blood vessels (Ido et al., *Science* 277: 563–66, 1997).

Chromosomal localization of the human Zins2 testis-specific insulin homolog polypeptide to chromosome 9p24 was determined using radiation hybrid chimeras. INSL4, another insulin homolog associated with reproductive tissue, was also mapped to chromosome 9p24 (Chassin et al., *Genomics* 29: 465–70, 1995). Relaxin 1 and 2 were mapped to 9pter-q12 (Grawford et al., *EMBO J.* 3: 2341–45, 1984). Several cases of sex reversal have been reported in association with de novo translocation or deletion involving 9p24 suggesting an association with this region and testis development (Hoo et al., *Am. J. Hum. Genet.* 45 (suppl.):A78, 1989; Bennett et al., *J. Med. Genet.* 30: 518–20, 1993).

Those skilled in the art will recognize that the sequences disclosed in SEQ ID NO: 1 and SEQ ID NO: 12 represent a single allele of the rat and human testis-specific insulin homolog polypeptide, respectively, and that allelic variation, "allelic variants", and alternative splicing, "splice variants", are expected to occur. Allelic variants of the DNA sequences shown in SEQ ID NO:1 and SEQ ID NO:12, including those containing silent mutations and those in which mutations result in amino acid sequence changes, are within the scope of the present invention, as are proteins which are allelic variants of SEQ ID NO:2 and SEQ ID NO:13. Splice variants of the DNA sequences shown in SEQ ID NO:1 and SEQ ID NO:12 include DNA sequences that result from mature RNA molecules created by known eukaryotic RNA splicing processes wherein intron sequence is removed and exon sequence is joined. Such DNA sequences encoding proteins which retain properties of the Zins2 testis-specific insulin homolog proteins of SEQ ID NO:2 and SEQ ID NO:13 are within the scope of the present invention. Allelic variants and splice variants of these sequences can be cloned by probing cDNA or genomic libraries from different individuals or tissues according to standard procedures known in the art.

The present invention further provides counterpart polypeptides and polynucleotides from other species ("species homologs"). These species would include, but are not limited to, mammalian, avian, amphibian, reptile, fish, insect and other vertebrate and invertebrate species. Of particular interest are testis-specific insulin homolog polypeptides from other mammalian species, including murine, porcine, ovine, bovine, canine, feline, equine and other primate proteins. Species homologs of relaxin are unique in that there is considerable structural variation between the species, possibly resulting in functional differences between the proteins from species to species. For example, between pig, rat and human relaxins the amino acid residues can vary by greater than 50% (U.S. Pat. No. 4,835,251, incorporated herein by reference.)

Alternate species polypeptides of zins2 may have importance therapeutically. It has been demonstrated that in some cases use of a non-native protein, i.e., protein from a different species, can be more potent than the native protein. For example, salmon calcitonin has been shown to be considerably more effective in arresting bone resorption than human forms of calcitonin. There are several hypotheses as to why salmon calcitonin is more potent than human calcitonin in treatment of osteoporosis. These hypotheses include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites. Another example is found in the β-endorphin family (Ho et al., *Int. J. Peptide Protein Res.* 29: 521–24, 1987). Studies have demonstrated that the peripheral opioid activity of camel, horse, turkey and ostrich β-endorphins is greater than that of human β-endorphins when isolated guinea pig ileum was electrostimulated and contractions were measured. Vas deferens from rat, mouse and rabbit were assayed as well. In the rat vas deferens model, camel and horse β-endorphins showed the highest relative potency. Synthesized rat relaxin was as active as human and porcine relaxin in the mouse symphysis pubis assay (Bullesbach and Schwabe, *Eur. J. Biochem.* 241: 533–7, 1996). Thus, the rat zins2 molecules of the present invention may have higher potency than the human endogenous molecule in human cells, tissues and recipients.

Species homologs of the rat and human testis-specific insulin homolog polypeptides can be cloned using information and compositions provided by the present invention, in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue cell line. A testis-specific insulin homolog-encoding cDNA can then be isolated by a variety of methods, such as by probing with a complete or partial rat cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the testis-specific insulin homolog protein or polypeptide. Similar techniques can also be applied to the isolation of genomic clones.

The present invention also provides isolated testis-specific insulin homolog polypeptides that are substantially homologous to the polypeptides of SEQ ID NO: 2, SEQ ID NO:13 and their species homologs. By "isolated" is meant a protein or polypeptide which is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 70%, more preferably at least 85%, sequence identity to the sequences shown in SEQ ID NO: 2, SEQ ID NO: 13, or their species homologs. Such polypeptides will more preferably be at least 90% identical, and most preferably 95% or more identical to SEQ ID NO: 2, SEQ ID NO: 13, or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89: 10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes).

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity of the optimal alignment is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, such as a polyhistidine tract, an antigenic epitope or a binding domain. See, in general Ford et al., *Protein Expression and Purification* 2: 95–107, 1991, which is incorporated herein by reference.

TABLE 2

Conservative amino acid substitutions

| | |
|---|---|
| Basic | arginine |
| | lysine |
| | histidine |
| Acidic | glutamic acid |
| | aspartic acid |
| Polar | glutamine |
| | asparagine |
| Hydrophobic | leucine |
| | isoleucine |
| | valine |
| Aromatic | phenylalanine |
| | tryptophan |
| | tyrosine |
| Small | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an *E. coli* S30 extract and commercially available enzymes and other reagents. Proteins are purified by chromatography. See, for example, Robertson et al., *J. Am. Chem. Soc.* 113: 2722, 1991; Ellman et al., *Meth. Enzymol.* 202: 301, 1991; Chung et al., *Science* 259: 806–09, 1993; and Chung et al., *Proc. Natl. Acad. Sci. USA* 90: 10145–49, 1993). In a second method, translation is carried out in *Xenopus* oocytes by microinjection of mutated mRNA and chemically aminoacylated suppressor tRNAs (Turcatti et al., *J. Biol. Chem.* 271: 19991–98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33: 7470–76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2: 395–403, 1993).

A limited number of non-conservative amino acids, amino acids that are not encoded by the genetic code, non-naturally occurring amino acids, and unnatural amino acids may be substituted for amino acid residues in the polypeptides of the present invention. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the polypeptides of the present invention can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity (e.g. proliferation or differentiation) to identify amino acid residues that are critical to the activity of the molecule.

Multiple amino acid substitutions can be made and tested using known methods of mutagenesis and screening, such as those disclosed by Reidhaar-Olson and Sauer (*Science* 241: 53–57, 1988) or Bowie and Sauer (*Proc. Natl. Acad. Sci. USA* 86: 2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30: 10832–10837, 1991; Ladner et al., U.S. Pat. No. 5,223,409; Huse, WIPO Publication WO 92/06204) and region-directed mutagenesis (Derbyshire et al., *Gene* 46: 145, 1986; Ner et al., *DNA* 7: 127, 1988).

Mutagenesis methods as disclosed above can be combined with high-throughput, automated screening methods to detect activity of cloned, mutagenized polypeptides in host cells. Mutagenized DNA molecules that encode active polypeptides (e.g., stimulation of proliferation or differentiation of testicular cells) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 1 to 188 of SEQ ID NO: 2, residues 1 to 213 of SEQ ID NO: 13, or allelic variants thereof and retain the activity of the wild-type protein.

The polypeptides of the present invention, including full-length proteins and fragments thereof, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly culture cells of multicellular organisms, are preferred. Techniques for manipulating cloned DNA molecules and introducing exogenous DNA into a variety of host cells are disclosed by Sambrook et al., *Molecular Cloning: A Labo-* ratory Manual, 2nd ed., Cold Spring Harbor Laboratory Press, Cold Spring Harbor, N.Y., 1989, and Ausubel et al., ibid., which are incorporated herein by reference.

In general, a DNA sequence encoding a testis-specific insulin homolog polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To insure cleavage of the B and A chains, cells transfected with expression vectors containing DNA sequences encoding testis-specific insulin homologs are co-transfected with expression vectors encoding a suitable prohormone convertase, for example furin, PC4, PC2 or PC3. Such sequences are known in the art and can be inserted into expression vectors and transfected into cells as described herein.

To direct a testis-specific insulin homolog polypeptide into the secretory pathway of a host cell, a secretory signal sequence (also known as a leader sequence, prepro sequence or pre sequence) is provided in the expression vector. The secretory signal sequence may be that of the testis-specific insulin homolog polypeptide, or may be derived from another secreted protein (e.g., t-PA) or synthesized de novo. The secretory signal sequence is joined to the testis-specific insulin homolog DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Patent No. 5,143,830).

Cultured mammalian cells are also preferred hosts within the present invention. Methods for introducing exogenous DNA into mammalian host cells include calcium phosphate-mediated transfection (Wigler et al., *Cell* 14: 725, 1978; Corsaro and Pearson, *Somatic Cell Genetics* 7: 603, 1981: Graham and Van der Eb, *Virology* 52: 456, 1973), electroporation (Neumann et al., *EMBO J.* 1: 841–845, 1982), DEAE-dextran mediated transfection (Ausubel et al., eds., *Current Protocols in Molecular Biology,* John Wiley and Sons, Inc., NY, 1987), and liposome-mediated transfection (Hawley-Nelson et al., *Focus* 15: 73, 1993; Ciccarone et al., *Focus* 15: 80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784, 950; Palmiter et al., U.S. Pat. No. 4,579,821; and Ringold, U.S. Pat. No. 4,656,134, which are incorporated herein by reference. Preferred cultured mammalian cells include BHK 570 cells (ATCC accession no.10314), COS-1 (ATCC No. CRL 1650), COS-7 (ATCC No. CRL 1651), 293 (ATCC No. CRL 1573; Graham et al., *J. Gen. Virol.* 36: 59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162, 222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci. (Bangalore)* 11: 47–58, 1987.

Fungal cells, including yeast cells, and particularly cells of the genus Saccharomyces, can also be used within the present invention, such as for producing testis-specific insulin homolog fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870, 008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondlii* and *Candida maltosa* are known in the art. See, for example, Gleeson et al., *J. Gen. Microbiol.* 132: 3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Testis-specific insulin homolog polypeptides can also be used to prepare antibodies that specifically bind to testis-specific insulin homolog epitopes, peptides or polypeptides. Methods for preparing polyclonal and monoclonal antibodies are well known in the art (see, for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a testis-specific insulin homolog polypeptide may be increased through the use of an adjuvant, such as alum (aluminum hydroxide) or Freund's complete or incomplete adjuvant. Polypeptides useful for immunization also include fusion polypeptides, such as fusions of testis-specific insulin homolog or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to testis-specific insulin homolog protein or peptide, and selection of antibody display libraries in phage or similar vectors (for instance, through use of immobilized or labeled testis-specific insulin homolog protein or peptide).

Antibodies are defined to be specifically binding if they bind to a testis-specific insulin homolog polypeptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to testis-specific insulin homolog proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant testis-specific insulin homolog protein or peptide.

Antibodies to testis-specific insulin homolog polypeptides may be used for tagging cells that express testis-specific insulin homolog polypeptides; for isolating testis-specific insulin homolog polypeptides by affinity purification; for diagnostic assays for determining circulating levels of testis-specific insulin homolog polypeptides; for detecting or quantitating soluble testis-specific insulin homolog polypeptides as marker of underlying pathology or disease; in analytical methods employing FACS; for screening expression libraries; for generating anti-idiotypic antibodies; and as neutralizing antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications.

Testis-specific insulin homolog polypeptide prepared according to the present invention is purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography, Q-Fast Flow Sepharose, MonoQ resin, FPLC, phenyl Sepharose, hydroxyapatite, Mono S and/or S-Sepharose. Proteins can also be purified using an immobilized an affinity tag (e.g., polyhistidine, substance P or other polypeptide or protein for which an antibody or other specific binding agent is available). A specific cleavage site may be provided between the protein of interest and the affinity tag. Preferred affinity tags include polyhistidine tail, which permits purification of the fusion protein on immobilized nickel (Houchuli et al., *Bio/Technol.* 6: 1321–1325, 1988). In prokaryotic expression systems, a maltose binding protein (MBP) fusion may be advantageously used as an affinity tag. If the protein is to be recovered from the cytoplasm or periplasm of the host cells, the cells are first disrupted, and a crude extract containing the protein is recovered and subjected to further purification steps.

Secreted protein is recovered from cell-conditioned media, preferably after concentration of the conditioned media. Selection of particular fractionation steps and the sequence of those steps will be based in part of the type of host cell and the expression system chosen. Such determinations are within the level of ordinary skill in the art.

Methods for preparing polyclonal and monoclonal antibodies are well known in the art (see for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of a testis-specific insulin homolog polypeptide may be increased through the use of an adjuvant such as Freund's complete or incomplete adjuvant.

Antibodies to testis-specific insulin homolog polypeptide may be used for isolating, for affinity purification, for diagnostic assays for determining circulating levels of testis-specific insulin homolog polypeptides, and as antagonists to block testis-specific insulin homolog binding and signal transduction in vitro and in vivo. These antibodies would be useful as contraceptives to prevent fertilization of an egg. Such antibodies could act as antagonists by inhibiting a component(s) of spermatogenesis and/or sperm activation. Such antibody "antagonists" can be used for contraception in animals, and in particular, domestic animals and livestock. For instance, anti-Zins2 immunization could be used in place of surgical forms of contraception (such as spaying and neutering), and would allow for the possibility of future breeding if desired.

Genes encoding polypeptides having potential Zins2 testis-specific insulin homolog polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zins2 testis-specific insulin homolog sequences disclosed herein to identify proteins which bind to Zins2. These "binding proteins" which interact with Zins2 testis-specific insulin homolog polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zins2 "antagonists" to block testis-specific insulin homolog binding and signal transduction in vitro and in vivo. These anti-Zins2 binding proteins would be useful for inhibiting spermatogenesis and sperm activation. Such anti-Zins2 binding proteins can be used for contraception in humans and animals, and in particular, domestic animals and livestock, where they act to prevent fertilization of an egg. Such anti-Zins2 binding proteins could be used, for instance, in place of surgical forms of contraception (such as spaying and neutering), and would allow for the possibility of future breeding of treated animals if desired.

A variety of assays known to those skilled in the art can be utilized to detect antibodies or binding proteins which specifically bind to testis-specific insulin homolog proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot or Western blot assays, inhibition or competition assays, and sandwich assays. A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145: 229–240, 1991 and Cunningham and Wells, *J. Mol. Biol.* 234: 554–563, 1993. A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Molecules of the present invention can be used to identify and isolate receptors for testis-specific insulin homolog polypeptides. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62: 483–514, 1993 and Fedan et al., *Biochem. Pharmacol.* 33: 1167–1180, 1984) and specific cell-surface proteins can be identified.

Polypeptides of the present invention are used to stimulate proliferation or differentiation of testicular cells. Proliferation and differentiation can be measured using cultured testicular cells or in vivo by administering molecules of the present invention to the appropriate animal model. Cultured testicular cells include dolphin DB1.Tes cells (CRL-6258); mouse GC-1 spg cells (CRL-2053); TM3 cells (CRL-1714); TM4 cells (CRL-1715); and pig ST cells (CRL-1746), available from American Type Culture Collection, 12301 Parklawn Drive, Rockville, Md. Assays measuring cell proliferation or differentiation are well known in the art. For example, assays measuring proliferation include such assays as chemosensitivity to neutral red dye (Cavanaugh et al., *Investigational New Drugs* 8: 347–354, 1990, incorporated herein by reference), incorporation of radiolabelled nucleotides (Cook et al., *Analytical Biochem.* 179: 1–7, 1989, incorporated herein by reference), incorporation of 5-bromo-2'-deoxyuridine (BrdU) in the DNA of proliferating cells (Porstmann et al., *J. Immunol. Methods* 82: 169–179, 1985, incorporated herein by reference), and use of tetrazolium salts (Mosmann, *J. Immunol. Methods* 65: 55–63, 1983; Alley et al., *Cancer Res.* 48: 589–601, 1988; Marshall et al., *Growth Reg.* 5: 69–84, 1995; and Scudiero et al., *Cancer Res.* 48: 4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5: 281–284, 1991; Francis, *Differentiation* 57: 63–75, 1994; Raes, *Adv. Anim. Cell Biol. Technol. Bioprocesses*, 161–171, 1989; all incorporated herein by reference).

In vivo assays for evaluating the effect of testis-specific insulin homolog polypeptide on testes are well known in the art. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99: 72–78, 1976; incorporated herein by reference).

Other activities, for example, chemotaxic activity that may be associated with proteins of the present invention can be analyzed. For example, late stage factors in spermatogenesis may be involved in egg-sperm interactions and sperm motility. Activities, such as enhancing viability of cryopreserved sperm, stimulating the acrosome reaction, enhancing sperm motility and enhancing egg-sperm interactions may be associated with the proteins of the present invention. Assays evaluating such activities are known (Rosenberger, *J. Androl.* 11: 89–96, 1990; Fuchs, *Zentralbl Gynakol* 11: 117–120, 1993; Neurwinger et al., *Andrologia* 22: 335–9, 1990; Harris et al., *Human Reprod.* 3: 856–60, 1988; and Jockenhovel, *Andrologia* 22: 171–178, 1990; Lessing et al., *Fertil. Steril.* 44: 406–9 (1985); Zaneveld, In Male Infertility Chapter 11, Comhaire Ed., Chapman & Hall, London 1996; all incorporated herein by reference). These activities are expected to result in enhanced fertility and successful reproduction.

Accordingly, proteins of the present invention may have applications in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who may have physiological or metabolic disorders that prevent natural conception. They may be used to enable women who wish to bear children but do not wish to, or are unable to conceive naturally. Such methods are also used in animal breeding programs, such as for livestock breeding and could be used as methods for the creation of transgenic animals. Proteins of the present invention can be combined with sperm, an egg or an egg-sperm mixture prior to fertilization of the egg. In some species, sperm capacitate spontaneously during in vitro fertilization procedures, but normally sperm capacitate over an extended period of time both in vivo and in vitro. It is advantageous to increase sperm activation during such procedures to enhance the likelihood of successful fertilization. The washed sperm or sperm removed from the seminal plasma used in such assisted reproduction methods has been shown to have altered reproductive functions, in particular, reduced motility and zona interaction. To enhance fertilization during assisted reproduction methods sperm is capacitated using exogenously added compounds. Suspension of the sperm in seminal plasma from normal subjects or in a "capacitation media" containing a cocktail of compounds known to activate sperm, such as caffeine, dibutyl cyclic adenosine monophosphate (dbcAMP) or theophylline, have resulted in improved reproductive function of the sperm, in particular, sperm motility and zonae penetration (Park et al., *Am. J. Obstet. Gynecol.* 158: 974–9, 1988; Vandevoort et al., Mol. Repro. Develop. 37: 299–304, 1993; Vandevoort and Overstreet, *J. Androl.* 16: 327–33, 1995). The presence of immunoreactive relaxin in vivo and in association with cryopreserved semen, was shown to significantly increase sperm motility (Juang et al., *Anim. Reprod. Sci.* 20: 21–9, 1989; Juang et al., *Anim. Reprod. Sci.* 22: 47–53, 1990). Porcine relaxin stimulated sperm motility in cryopreserved human sperm (Colon et al., *Fertil. Steril.* 46: 1133–39, 1986; Lessing et al., *Fertil. Steril.* 44: 406–9, 1985) and preserved ability of washed human sperm to penetrate cervical mucus in vitro (Brenner et al., *Fertil. Steril.* 42: 92–6, 1984, all incorporated herein by reference). Polypeptides of the present invention can used in such methods to enhance viability of cryopreserved sperm, enhance sperm motility and enhance fertilization, particularly in association with methods of assisted reproduction.

In cases where pregnancy is not desired, Zins2 proteins or protein fragments may function as germ-cell-specific antigens for use as components in "immunocontraceptive" or "anti-fertility" vaccines to induce formation of antibodies and/or cell mediated immunity to selectively inhibit a process, or processes, critical to successful reproduction in humans and animals. The use of sperm and testis antigens in the development of an immunocontraceptive have been described (O'Hern et al., *Biol Reprod.* 52: 311–39, 1995; Diekman and Herr, *Am. J. Reprod. Immunol.* 37: 111–17, 1997; Zhu and Naz, *Proc. Natl. Acad. Sci. USA* 94: 4704–9, 1997, all of which are incorporated herein by reference). A vaccine based on human chorionic gonadotrophin (HOG) linked to a diphtheria or tetanus carrier is currently in clinical trials (Talwar et al., *Proc. Natl. Acad. Sci. USA* 91: 8532–36, 1994, incorporated herein by reference). A single injection resulted in production of high titer antibodies that persisted for nearly a year in rabbits (Stevens, *Am. J. Reprod. Immunol.* 29: 176–88, 1993, incorporated herein by reference). Such methods of immunocontraception using vaccines would include a Zins2 testes-specific insulin homolog protein or fragment thereof. The Zins2 protein or fragments can be conjugated to a carrier protein or peptide, such as tetanus or diphtheria toxoid. An adjuvant, as described above, can be included and the protein or fragment can be noncovalently associated with other molecules to enhance intrinsic immunoreactivity. Methods for administration and methods for determining the number of administrations are known in the art. Such a method might include a number of primary injections over several weeks followed by booster injections as needed to maintain a suitable antibody titer.

Regulation of reproductive function in males and females is controlled in part by feedback inhibition of the hypothalamus and anterior pituitary by blood-bone hormones. Testis proteins, such as activins and inhibins, have been shown to regulate secretion of active molecules including follicle stimulating hormone (FSH) for the pituitary (Ying, *Endodcr. Rev.* 9: 267–93, 1988; Plant et al., *Hum. Reprod.* 8: 41–44, 1993). Inhibins, also expressed in the ovaries, have also been shown to regulate ovarian functions (Woodruff et al., *Endocr.* 132: 2332–42, 1993; Russell et al., *J. Reprod. Fertil.* 100: 115–22, 1994). Relaxin has also been shown to be a systemic and local acting hormone regulating follicular and uterine growth (Bagnell et al., *J. Reprod. Fertil.* 48: 127–38, 1993), as such, the polypeptides of the present invention may also have effects on female gametes and reproductive tract. These functions may also be associated with the Zins2 proteins and may be used to regulate testicular or ovarian functions.

For pharmaceutical use, the polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a testis-specific insulin homolog polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences,* Gennaro, ed., Mack Publishing Co., Easton Pa., 1990, which is incorporated herein by reference. Therapeutic doses will generally be in the range of 0.1 to 100 pg/kg of patient weight per day, preferably 0.5–20 µg/kg per day, with the exact dose determined by the clinician according to accepted standards, taking into account the nature and severity of the condition to be treated, patient traits, etc. Determination of dose is within the level of ordinary skill in the art. The polypeptides may be administered for acute treatment, over one week or less, often over a period of one to three days or may be used in chronic treatment, over several months or years.

EXAMPLES

Example 1

A.

Scanning of a cDNA database for sequences structurally homologous to insulin revealed an expressed sequence tag (EST) from a human testis cDNA library that is homologous to relaxin, with the homology spanning nucleotides 1–189 of SEQ ID NO: 8. This EST encoded a secretory signal sequence followed by the insulin, family B chain motif. Analysis of the sequence revealed a putative amphipathic helix, providing additional confirmation of an insulin B chain homology.

B.

The rat first strand cDNA reaction contained 10 µl of rat testis poly d(T)-selected poly (A)$^+$ mRNA (Clontech, Palo Alto, Calif.) at a concentration of 1.0 µg/µl, and 2 µl of 20 pmole/µl first strand primer ZC6091 (SEQ ID NO: 3) containing an Xho I restriction site. The mixture was heated at 70° C. for 4 minutes and cooled by chilling on ice. First strand cDNA synthesis was initiated by the addition of 8 µl of first strand buffer (5× SUPERSCRIPT™ buffer; Life Technologies, Gaithersburg, Md.), 4 µl of 100 mM dithiothreitol, and 2 µl of a deoxynucleotide triphosphate solution containing 10 mM each of DATP, dGTP and 5-methyl-dCTP (Pharmacia LKB Biotechnology, Piscataway, N.J.) to the RNA-primer mixture. The reaction mixture was incubated at 45° C. for 2 minutes, followed by the addition of 10 µl of 200 U/µl RNase H-reverse transcriptase (SUPERSCRIPT II®; Life Technologies). The efficiency of the first strand synthesis was analyzed in a parallel reaction by the addition of 10 µCi of $^{32}$P-αdCTP to 5 µl aliquot from one of the reaction mixtures to label the reaction for analysis. The reactions were incubated at 45° C. for 1 hour followed by an incubation at 50° C. for 10 minutes. Unincorporated $^{32}$P-αdCTP in the labeled reaction was removed by chromatography on a 400 pore size gel filtration column (Clontech). The unincorporated nucleotides and primers in the unlabeled first strand reactions were removed by chromatography on 400 pore size gel filtration column (Clontech). The length of labeled first strand cDNA was determined by agarose gel electrophoresis.

The second strand reaction contained 102 µl of the unlabeled first strand cDNA, 30 µl of 5× polymerase I buffer (125 mM Tris: HCl, pH 7.5, 500 mM KCl, 25 mM MgCl$_2$, 5 mM (NH$_4$)$_2$SO$_4$)), 2 µl of 100 mM dithiothreitol, 3 µl of a solution containing 10 mM of each deoxynucleotide triphosphate, 5 µl of 5 mM β-NAD, 2 µl of 3 U/µl *E. coli* DNA ligase (New England Biolabs, Inc., Beverly, Mass.), 5 µl of 10 U/µl *E. coli* DNA polymerase I (New England Biolabs), and 1.5 µl of 2 U/µl RNase H (Life Technologies). A 10 µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 10 µl T4 DNA polymerase (10 U/µl, Boehringer Mannheim, Indianapolis, Ind.) and incubated for an additional 5 minutes at 16° C. Unincorporated $^{32}$P-αdCTP in the labeled reaction was removed by chromatography through a 400 pore size gel filtration column (Clontech) before analysis by agarose gel electrophoresis. The unlabeled was terminated by the addition of 20 µl 0.5 M EDTA and extraction with phenol/ chloroform and chloroform followed by ethanol precipitation in the presence of 2.5 M ammonium acetate. The yield of cDNA was estimated to be approximately 2 µg from starting mRNA template of 10 µg.

Eco RI adapters were ligated onto the 5' ends of the cDNA described above to enable cloning into an expression vector. A 10.5 µl aliquot of cDNA (~2 µg) and 5 µl of 65 pmole/µl of Eco RI adapter (Pharmacia LKB Biotechnology Inc.) were mixed with 2.5 µl 10× ligase buffer 66 mM Tris-HCl pH 7.5, 10 mM MgCl$_2$, 2.5 µl of 10 mM ATP and 1 µl of 15 U/µl T4 DNA ligase (Promega Corp., Madison, Wis.). The reaction was incubated overnight (~12 hours) at 12° C. The reaction was terminated by incubation at 70° C. for 20 minutes. After incubation, the reaction was cooled to 37° C. To the reaction was added 2.5 µl 10 mM ATP and 3 µl 10 U/µl T4 polynucleotide kinase (Life Technologies) to phosphorylate the ligated Eco RI adapters.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO: 3). Restriction enzyme digestion was carried out in a reaction mixture containing 25 µl of cDNA described above, 15 µl of 10× H Buffer (Boehringer Mannheim), 109 µl H$_2$O, and 1.0 µl of 40 U/µl Xho I (Boehringer Mannheim). Digestion was carried out at 37° C. for 40 minutes. The reaction was terminated by incubation at 65° C. for 10 minutes and chromatography through a 400 pore size gel filtration column (Clontech).

The cDNA was ethanol precipitated, washed with 70% ethanol, air dried and resuspended in 20 µl of 1× gel loading buffer (10 mM Tris: HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 µl) and 35 µl 10× β-agarose I buffer (New England Biolabs) was added to the tube, and the agarose was melted by heating to 65° C. for 15 minutes. Following equilibration of the sample to 45° C., 3 µl of 1 U/µl β-agarose I (New England Biolabs) was added, and the mixture was incubated for 60 minutes at 45° C. to digest the agarose. After incubation, 40 µl of 3 M Na acetate was added to the sample, and the mixture was incubated on ice for 15 minutes. The sample was centrifuged at 14,000× g for 15 minutes at room temperature to remove undigested agarose. The cDNA was ethanol precipitated, washed in 70% ethanol, air-dried and resuspended in 10 µl water.

The resulting cDNA was cloned into the lambda phage vector λZap® II that was predigested with Eco RI and Xho I and dephosphorylated (Stratagene Cloning Systems, La Jolla, Calif.). Ligation of the cDNA to the λZap® II vector was carried out in a reaction mixture containing 1.0 µl of prepared vector, 1.0 µl of rat testis cDNA, 1.0 µl 10× Ligase Buffer (Promega), 1.0 µl of 10 mM ATP, 5 µl water, and 1.0 µl of T4 DNA Ligase at 15 units/ml (Promega). The ligation mixture was incubated at 5° C.–15° C. overnight in a temperature gradient. After incubation, the ligation mixture was packaged into phage using GIGPACK® III GOLD packaging extract (Stratagene Cloning Systems) and the resulting library was titered according to the manufacturer's specifications.

C.

The rat testis λZap® II library was used to infect XLI Blue MRF' host cells (Stratagene Cloning Systems), and 2×10⁶ pfu were plated onto 45 150-mm NZY plates. The inoculated plates were incubated overnight at 37° C. Filter plaques lifts were made using HYBOND-N nylon membranes (Amersham, Arlington Heights, Ill.), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 1 M Tris-HCl, pH 7.5, and 1.5 M NaCl. Phage DNA was fixed onto the filters with 1,200 µjoules of UV energy in a STRATALINKER® UV Crosslinker (Stratagene Cloning Systems). After fixing, the filters were prehybridized in hybridization solution (5× SSC, 5× Denhardt's solution, 0.2% SDS and 1 mM EDTA). Heat denatured, sheared salmon sperm DNA at a final concentration of 100 µg/ml was added. The filters were prehybridized at 65° C. overnight.

A probe was prepared as a PCR product by using oligonucleotide primers designed to amplify the human testis-specific insulin homolog cDNA coding region (see Example 5). A PCR reaction mixture containing 2 µl of ZC10008 (SEQ ID NO: 4) and 2 µl of ZC10491 (SEQ ID NO: 5) 1 µl of 100 fentogram pSLHIT-10 (described in Example 5), 1 µl of 10 mM dNTPs, 10 µl of 10× KlenTaq buffer (Clontech), 82 µl water, and 2 µl KlenTaq DNA polymerase (Clontech). The PCR reaction was run as follows: 1 cycle at 94° C. for 1 minute; 30 cycles at 95° C. for 20 seconds, 60° C. for 20 seconds, 68° C. for 1 minute; and 1 cycle at 68° C. for 10 minutes. The PCR product was gel purified on a 1.5% low melt agarose gel.

Fifty nanograms PCR product was radiolabeled with $^{32}$P dCTP by random priming using the MEGAPRIME™ DNA Labeling System (Amersham), according to the manufacturer's specifications. The prehybridization solution was replaced with fresh hybridization solution containing 1.4× 10⁶ cpm/ml labeled probe and allowed to hybridize for 64 hours at 60° C. After hybridization, the hybridization solution was removed and the filters were rinsed in a wash solution containing 1× SSC, 0.25% SDS and 1 mM EDTA at 45° C. The filters were placed on autoradiograph film and exposed at −70° C. with intensifying screens for 96 hours.

Examination of the autoradiographs revealed 134 regions that hybridized with the labeled probe. Agar plugs were picked from 73 regions for purification. Each agar plug was soaked overnight in 1 ml of SM containing 1% (v/v) chloroform (Sambrook et al. *Molecular Cloning: A Laboratory Manual*, 2nd ed., Cold Spring Harbor Laboratory Press, Cold Spring Harbor, N.Y., 1989). After incubation, the phage from each plug were diluted 1:1000 in SM. Aliquots of 12.5 µl were plated on *E. coli* XL-1 Blue MRF' cells. The plates were incubated overnight at 37° C., and filter lifts were prepared, prehybridized, hybridized, washed and autoradiographed as described above. Examination of the resulting autoradiographs revealed positive signals on 3 filter lifts.

The plasmids were excised using an ExASSIST/SOLR™ system (Stratagene Cloning Systems), according to the manufacturer's specification. These plasmids were amplified by PCR for insert size determination and sequencing. A clone, designated pSLRatzins2-1, was shown to have a 0.79 kb insert and contained the sequence shown in SEQ ID NO: 1.

Example 2

A probe was prepared from the full length coding sequence of Zins2 and used to probe Human Multiple Tissue Northern Blots (Clontech). The Northern analysis revealed a band at approximately 1.2 kb that was only present in testis.

Example 3

In situ hybridization was done to localize expression of Zins2 polypeptide within the testis.

A.

Oligonucleotide primers were designed to begin priming at the ATG and introduce a Sal I cloning site (ZC10008; SEQ ID NO: 4; and ZC10491; SEQ ID NO: 5), designed to begin priming immediately downstream from the termination codon sequence, eliminating the 3' non-coding region and introducing a Xba I cloning site. Template for the PCR was testis cDNA and the reaction was done as follows: 1 µl template DNA; 10 µl KlenTaq buffer (Clontech); 1 µl of 10 mM dNTPs; 2 µl of each ZC10008 (SEQ ID NO: 4) and ZC10491 (SEQ ID NO: 5); 87 µl of H₂O and 1 µl of KlenTaq Polymerase (Clontech) were mixed and run for 20 cycles at 95° C. for 30 seconds, 60° C. for 30 seconds and 68° C. for 2 minutes. The resulting PCR product was phenol-chloroform extracted and DNA was precipitated with ethanol and resuspended. The resuspended DNA was digested with Sal I and Xba I and ligated into pBluescript SK+® phagemid vector (Stratagene).

An antisense riboprobe was prepared utilizing the T7 polymerase promoter of the vector. 30 µl of pSLHIT-7 was digested with 150 units of Xba I and phenol-chloroform extracted, precipitated in ethanol and resuspended in water. A sense riboprobe was prepared utilizing the T3 polymerase promoter by digesting 30 µl of pSLHIT-7 with 200 units of Xho I, and then phenol-chloroform extracted, precipitated in ethanol and resuspended in water.

Labeling of the DNA was done in the following reaction: 1 µg of DNA in a 20 µl volume of water, 2 µl of 10× transcription buffer (Ambion, Austin, Tex.); 1 µl of 10 mM each, ATP, CTP, and GTP; 5 µl $^{35}$S UTP at 1000 Ci/mmol at 12,500 mCi/ml (Amersham) and 2 µl T3 or T7 polymerase (Ambion) were mixed and incubated at 37° C. for 1 hour. After incubation, the reactions were centrifuged and 50 µl of SET-DTT (100 µl 10% SDS; 10 µl of 1 M Tris, pH 7.5; 2 µl of 0.5 M EDTA, pH 8.0; 10 µl of 1 M DTT; 878 µl of water) was added to each tube and the reactions were incubated at 65° C. for 5 min. The reaction mixtures were centrifuged and 1 µl/reaction was analyzed for cpm. The remaining (69 µl) of the reaction was purified over a Sephadex G-50 spin column (Pharmacia). The resulting probes were $1.8 \times 10^6$ cpm/µl for the antisense probe and $8.9 \times 10^6$ cpm/µl for the sense probe.

B.

Testis tissue was prepared for in situ hybridization using techniques known in the art. See, for example, Simmons et al., *J. of Histotechnology* 12: 169–181, 1989; and Sylvester et al., *Biol. of Reproduction* 45: 195–207, 1991.

Briefly, Macaque monkey testicular tissue was prepared as follows:

Twenty minutes prior to perfusion with saline and fixatives, the monkey was perfused with heparin.

Tubing was primed with saline (9% NaCl) and fixatives (see Tables 4 and 5), with fixatives held on ice and saline at room temperature.

TABLE 4

| Fix A | 50 ml |
|---|---|
| NaOH | 0.20 g |
| paraformaldehyde | 2 g |
| Na Acetate, trihydrate | 1.13 g |
| Adjust pH to 6.5 and use at 4° C. | |

TABLE 5

| Fix B | 50 ml |
|---|---|
| NaOH | 0.2 g |
| paraformaldehyde | 2 g |
| Na Tetraborate-10 H$_2$O | 1.91 |
| Adjust the pH to 9.5 and store at 4° C. | |
| Fix C with 10% sucrose | |
| Place 2 g of sucrose in a 50 ml conical centrifuge tube, then add fix B to 20 ml. | |

At time zero, the monkey was injected with sodium pentobarbitol, and when the animal no longer responded to pinching of the foot pad, the surgical procedure was begun.

The chest cavity opened to the diaphragm to clear the working field. A blunted 18 g needle (attached to tubing filled with saline) was inserted into the left ventricle. Once the heart swelled the right atrium was clipped. The pump setting to was adjusted gradually to a rate of 40 ml/min.

The testes were exposed, watching for the bleaching of the testicular artery and testicular vein, an indication that blood is being replaced by saline.

After the testes were bleached, the pump was switched from saline over to Fix A. Muscle twitching or contraction was used as an indication that fixing had begun. 250 ml Fix A at 40 ml/min was perfused into the animal. After perfusion with Fix A was completed, the pump was switched to Fix B for 5 minutes at 40 ml/min, and then reduced to a rate of 20 ml/min until 400–450 ml Fix B was perfused.

The testes were excised and stored in Fix C, overnight at 4° C.

C.

Slides of cross sections of Macaque testes were prepared for hybridization as follows:

The slides were deparaffinized by immersing in xylene 2 times, 10 min. After deparaffinizing, the slides were rehydrated by immersing in decreasing concentrations of ethanol solutions (100%, 99%, 95%, 85%, 70%, 50%, 30%) for 2 minutes each.

The slides were treated with pre-heated Proteinase K solution (20 µl 20 mg/ml Proteinase K, 40 ml of 0.5 M EDTA, pH 8.0, 320 ml sterile H$_2$O) at 37° C. for 30 minutes. The slides were rinsed in sterile H$_2$O, 2 min. and then slides were rinsed in 0.1 M triethanolamine, pH 8.0, 3 min. The slides were rinsed in acetylation solution (500 µl acetic anhydride, 200 ml of 0.1 M Triethanolamine), 10 min. The slides were rinsed twice, 2 min in 2× SSC.

The tissue was dehydrated by immersing slides in increasing concentrations of ethanol solutions (in the reverse order to the listed above) and then dried under vacuum with desiccant for 1½ hours.

D.

Prepared Macaque testis slides were hybridized in a solution containing: 2.5 ml of 100% deionized formamide (50%), 10% dextran sulfate, 3 M NaCl, 1× Denhardt's solution, 100 mM Tris, pH 8.0, 20 µl of 10 mg/ml salmon sperm DNA (40 ug/ml), and 100 mM DTT. Probes (as described in Example 3A) were added for a final volume of radioactivity of $1.67 \times 10^7$ cpm/ml.

70 µl total probe was added (approximately $1.2 \times 10^6$ cpm/slide) and overlayed each slide with parafilm. The slides were hybridized overnight at 50° C. in a moist slide chamber.

E.

After incubation, slides were placed in 4× SSC for about 30 minutes to loosen parafilm.

The parafilm was removed, and the slides were washed in 4× SSC 3 times, 5 minutes each, and then treated with RNase solution (20 µg RNase A, 0.5 M NaCl, 10 mM Tris:HCl pH 8.0, 1 mM EDTA pH 8.0).

The RNase solution was preheated to 37° C. and slides were incubated in the RNase solution for 30 minutes at 37° C. After incubation, the slides were washed twice in 2× SSC/10 mM DTT for 10 minutes each at RT, once in 1× SSC/10 mM DTT for 10 minutes at RT, and once in 0.5× SSC/10 mM DTT for 10 minutes at RT. The slides were washed for 30 minutes at 60°–65° C. in preheated 0.1× SSC/10 mM DTT.

The tissue samples were dehydrated using ethanol solutions series of 30%, 50%, 70%, 85%, 95%, 99%, and 100%. After dehydration, the slides were drained well and place under vacuum with desiccant for 1 hour.

F.

Slides were treated with photographic emulsion by dipping pre-warmed (40° C.) slides into melted (42° C.) Kodak NTB2 Emulsion (Kodak, Rochester, N.Y.), allowing slides to dry, then storing them in light-tight, sealed containers with desiccant at 4° C.

Slides were developed at several intervals following emulsion by warming to room temperature, immersing in full strength Kodak D-19 developer (Kodak), rinsing 8 times in water, immersing 10 min. in Kodak fixer (Kodak), and dipping in water 8 times.

Slides were stained as follows:

1½ min. in hematoxylin solution, 5 min. in sterile water, 5 brief rinses in 95 ethanol, 1 min. in 0.1% Eosin Y, 2 min in sterile water, 8 brief rinses in 95% ethanol, 2 min. in 95% ethanol, 8 brief rinses in 100% ethanol, 2 min. in 100% ethanol, 8 brief rinses in xylene, 2 min. in xylene.

Slides were re-dipped in xylene then overlayed with a small amount of Permount (Fisher SP15-100) and covered with coverslips and viewed under microscope for silver grains showing distribution of zins2 (with anti-sense probe) vs. negative control (sense probe). Zins2 mRNA was found by in situ hybridization to be localized in the seminiferous tubules and epidymus.

Example 4

Zins2 was mapped to human chromosome 9 by PCR using the Human/Rodent Somatic Cell Hybrid Mapping Panel Number 2 (National Institute of General Medical Sciences, Coriell Institute of Medical Research, Camden, N.J.). The panel consists of DNA isolated from 24 human/rodent somatic cell hybrids each retaining one specific human chromosome and the parental DNAS. Specific Zins2 oligonucleotide primers, sense, ZC10684, (SEQ ID NO: 6), and antisense, ZC10685, (SEQ ID NO: 7), were used for PCR amplification. PCR conditions were as follows: an initial 1 cycle 5 minute denaturation at 95° C., 35 cycles of a 30 second denaturation at 95° C., 2 minute annealing at 68° C. and 30 second extension at 72° C., followed by a final 1 cycle extension of 8 minutes at 72° C. Each 50 µl PCR reaction consisted of 5 µl 10× KlenTaq PCR reaction buffer (CLONTECH Laboratories, Inc., Palo Alto, Calif.), 4 µl dNTPs mix (2.5 mM each, PERKIN-ELMER, Foster City, Calif.), 2.5 µl of (20 picomole/µl) ZC10684 (SEQ ID NO: 6), 2.5 µl of (20 picomole/µl) ZC10685 (SEQ ID NO: 7), 25 µl PCR-grade ddH20, 1 µl 50× Advantage KlenTaq Polymerase Mix (CLONTECH Laboratories, Inc.), and 10 µl DNA from the respective human/rodent somatic cell hybrid (10 ng/µl). The reactions were separated by electrophoresis on a 3% NuSieve GTG agarose gel (FMC Bioproducts, Rockland, Me.). The results demonstrated that Zins2 mapped to human chromosome 9.

Zins2 was further mapped to chromosome 9p24 using the commercially available version of the Whitehead Institute/MIT Center for Genome Research's GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zins2 with the GeneBridge 4 RH Panel, 25 µl reactions were set up in a PCRable 96-well microtiter plate (Stratagene, La Jolla, Calif.) and used in a RoboCycler Gradient 96 thermal cycler (Stratagene). Each of the 95 PCR reactions consisted of 2.5 µl 10× KlenTaq reaction buffer (Clontech), 2 µl dNTPs mix (2.5 mM each, Perkin-Elmer, Foster City, Calif.), 1.25 µl sense primer, ZC 10,684 (SEQ ID NO: 6), 1.25 µl antisense primer, ZC 10,685 (SEQ ID NO: 7), 2.5 µl RediLoad (Research Genetics), 0.5 µl 50× Advantage KlenTaq Polymerase Mix (Clontech), 25 ng of DNA from an individual hybrid clone or control and ddH20 for a total volume of 25 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 70° C. and 1 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that Zins2 maps 13.70 cR_3000 from the top of the human chromosome 9 linkage group on the WICGR radiation hybrid map. Proximal and distal framework makers were CHLC.GCT3G05 and D9S178, respectively. The use of surrounding markers positions Zins2 in the 9p24 region on the integrated LDB chromosome 9 map (The Genetic Location Database, University of Southampton, WWW server: http://cedar.genetics.soton.ac.uk/public_html/).

Example 5

Oligonucleotide primers were designed to begin priming at the putative start codon of the EST sequence and included sequence to encode a Kozak translational consensus sequence upstream of the start codon and a Sal I cloning site. The template for the PCR was Marathon Ready human testis cDNA (Clontech, Palo Alto, Calif.). The conditions for the PCR were as follows: 5 µl template cDNA; 10 µl KlenTaq 10× buffer; 1 µl 10 mM dNTPs; 1 µl of 20 pmole/µl ZC10008 (SEQ ID NO: 4); 2 µl of 10 pmole/µl AP-1 primer (Clontech); 79 µl H$_2$O and 2 µl KlenTaq polymerase. The reaction was run for 30 cycles at 95° C. for 30 seconds and 68° C. for 2 minutes.

The amplified DNA was gel purified in low melt agarose and a 700 base pair band was seen. Sequence analysis of the band determined that the PCR product duplicated the EST sequence and that the cDNA sequence was a full-length sequence with a 202 base pair 3' untranslated sequence as shown in SEQ ID NO: 8. The cDNA was designated Zins2. The PCR product was digested with Sal I and Eco RI and ligated with the Sal I and Eco RI digested expression vector pHZ-200.

pHZ-200 is the same as pHZ-1 with the exception that the dihydrofolate reductase sequence was substituted for the neomycin resistance gene. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an E. coli origin of replication; a bacterial beta lactamase gene; a mammalian selectable marker expression unit comprising the SV40 promoter and origin, a neomycin resistance gene and the SV40 transcription terminator. The plasmids resulting from the ligation reaction were designated pSLHIT-1, 2, 3, and 4.

Oligonucleotide primers were designed to hybridize to the 5' and 3' ends of the coding region of Zins2 (ZC10009, SEQ ID NO: 9 and ZC10537, SEQ ID NO: 10). Using a human testis cDNA library as template, PCR was performed as follows: parallel reaction mixtures containing 1 µl template DNA (25 ng), 2 µl of 20 pmole/µl ZC10009 (SEQ ID NO: 9) and ZC10537 (SEQ ID NO: 10), 1 µl of 10 mM dNTPs, 1 µl of 2.5 u/µl Native Pfu polymerase (Stratagene), 10 µl of 10× native Pfu buffer (Stratagene) were combined. The reaction was run for 25 cycles at 95° C. for 30 seconds, 55° C. or 50° C. for 30 seconds, 72° C. for 1 minute and followed by a 5 minute incubation at 72° C. The PCR products from the parallel reactions were gel purified and pooled.

The pooled PCR products were diluted 1:10 and 1:100 and used as template for another PCR reaction, where oligonucleotides were designed to incorporate restriction sites at the 5' and 3' ends of the Zins2 coding region. The reaction mixture contained 1 µl of either 1:10 or 1:100 template, 2 µl of 20 pmole/µl of each ZC10008 (SEQ ID NO: 4) or ZC10538 (SEQ ID NO: 11), 1 µl of 10 mM dNTPs, 10 µl of 10× Native Pfu Buffer (Stratagene), 1 µl of 2.5 u/µl Native Pfu polymerase (Stratagene) and 83 µl water were combined. The reaction was run for 3 cycles at 95° C. for 30 seconds, 40° C. for 30 seconds, 72° C. for 1 minute; 20 cycles at 95° C. for 30 seconds, 47° C. for 30 seconds, 72° C. for 1 minute; followed by a 5 minute incubation at 72° C.

The PCR products were pooled and digested with Proteinase K, phenol-chloroform extracted, ethanol precipitated and resuspended in water. The PCR products were gel purified on 10% low melt agarose. The DNA was digested with Sal I and Eco RI and ligated in Sal I/Eco RI digested pHZ-200. The resulting plasmid was designated pSLHIT-10 and was sequence analyzed.

Example 6

A full-length human Zins2 cDNA was obtained by screening a λZAP® human testis cDNA. The construction of the testis cDNA library was as follows: The first strand cDNA reaction contained 15 µl of human testis twice poly d(T)-selected poly (A)+ mRNA (Clontech) at a concentration of 1.0 µg/µl, and 3 µl of 20 pmole/µl first strand primer ZC6091 (SEQ ID NO: 3) containing an Xho I restriction site. The mixture was heated at 70° C. for 4 minutes and cooled by chilling on ice. First strand cDNA synthesis was initiated by the addition of 12 µl of first strand buffer (5× SUPERSCRIPT™ buffer; Life Technologies, Gaithersburg, Md.), 6 µl of 100 mM dithiothreitol, and 3 µl of a deoxynucleotide triphosphate solution containing 10 mM each of dTTP, DATP, dGTP and 5-methyl-dCTP (Pharmacia LKB Biotechnology, Piscataway, N.J.) to the RNA-primer mixture. The reaction mixture was incubated at 37° C. for 2 minutes, followed by the addition of 15 µl of 200 U/µl RNase H⁻ reverse transcriptase (SUPERSCRIPT II®; Life Technologies). The efficiency of the first strand synthesis was analyzed in a parallel reaction by the addition of 5 µCi of $^{32}$P-αdCTP to 5 µl aliquot from one of the reaction mixtures to label the reaction for analysis. The reactions were incubated at 37° C. for 10 minutes, 45° C. for 1 hour, then incubated at 50° C. for 10 minutes. Unincorporated $^{32}$P-αdCTP in the labeled reaction was removed by chromatography on a 400 pore size gel filtration column (Clontech Laboratories). The unincorporated nucleotides and primers in the unlabeled first strand reactions were removed by chromatography on 400 pore size gel filtration column (Clontech). The length of labeled first strand cDNA was determined by agarose gel electrophoresis.

The second strand reaction contained 120 µl of the unlabeled first strand cDNA, 36 µl of 5× polymerase I buffer (125 mM Tris: HCl, pH 7.5, 500 mM KCl, 25 mM $MgCl_2$, 50 mM $(NH_4)_2SO_4$)), 2.4 µl of 100 mM dithiothreitol, 3.6 µl of a solution containing 10 mM of each deoxynucleotide triphosphate, 6 µl of 5 mM β-NAD, 3.6 µl of 3 U/µl *E. coli* DNA ligase (New England Biolabs; Beverly, Mass.), 9 µl of 10 U/µl *E. coli* DNA polymerase I (New England Biolabs), and 1.8 µl of 2 U/µl RNase H (Life Technologies). A 10 µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 15 µl T4 DNA polymerase (10 U/µl, Boehringer Mannheim, Indianapolis, Ind.) and incubated for an additional 5 minutes at 16° C. Unincorporated $^{32}$P-αdCTP in the labeled reaction was removed by chromatography through a 400 pore size gel filtration column (Clontech) before analysis by agarose gel electrophoresis. The unlabeled was terminated by the addition of 20 µl 0.5 M EDTA and extraction with phenol/chloroform and chloroform followed by ethanol precipitation in the presence of 2.5 M ammonium acetate and 4 µg of glycogen carrier. The yield of cDNA was estimated to be approximately 3 µg from starting mRNA template of 15 µg.

Eco RI adapters were ligated onto the 5' ends of the cDNA described above to enable cloning into an expression vector. A 10 µl aliquot of cDNA (~1.5 µg) and 5 µl of 65 pmole/µl of Eco RI adapter (Pharmacia LKB Biotechnology Inc.) were mixed with 2 µl 10× ligase buffer (660 mM Tris-HCl pH 7.5, 100 mM $MgCl_2$), 2 µl of 10 mM ATP and 1 µl of 15 U/µl T4 DNA ligase (Promega Corp., Madison, Wis.). The reaction was incubated 2 hours at 5° C., two hours at 7.5° C., 2 hours at 10° C., and 10 hours at 12.5° C. The reaction was terminated by incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO: 3). Restriction enzyme digestion was carried out in a reaction mixture containing 20 µl of cDNA described above, 10 µl of 10× H Buffer (Boehringer Mannheim), 69 µl $H_2O$, and 1.0 µl of 40 U/µl Xho I (Boehringer Mannheim). Digestion was carried out at 37° C. for 40 minutes. The reaction was terminated by incubation at 70° C. for 10 minutes and chromatography through a 400 pore size gel filtration column (Clontech Laboratories).

The cDNA was ethanol precipitated, washed with 70% ethanol, air dried and resuspended in 14 µl water, 2 µl of ligase buffer (Promega Corp., Madison Wis.), 2 µl T4 polynucleotide kinase (10 U/µl, Life Technologies). Following incubation at 37° C. for 30 minutes, the cDNA was heated to 65° C. for 5 minutes, cooled on ice, and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 µl) and 35 µl 10× β-agarose I buffer (New England Biolabs) was added to the tube, and the agarose was melted by heating to 65° C. for 15 minutes. Following equilibration of the sample to 45° C., 3 µl of 1 U/µl β-agarose I (New England Biolabs) was added, and the mixture was incubated for 60 minutes at 45° C. to digest the agarose. After incubation, 40 µl of 3 M Na acetate was added to the sample, and the mixture was incubated on ice for 15 minutes. The sample was centrifuged at 14,000× g for 15 minutes at room temperature to remove undigested agarose. The cDNA was ethanol precipitated, washed in 70% ethanol, air-dried and resuspended in 10 µl water.

The resulting cDNA was cloned into the lambda phage vector λZap® II (Stratagene Cloning Systems) that was predigested with Eco RI and Xho I and dephosphorylated. Ligation of the cDNA to the λZap® II vector was carried out in a reaction mixture containing 1.0 µl of prepared vector, 1.0 µl of human testis cDNA, 1.0 µl 10× Ligase Buffer (Promega Corp.), 1.0 µl of 10 mM ATP, 5 µl water, and 1.0 µl of T4 DNA Ligase at 15 units/ml (Promega Corp.). The ligation mixture was incubated at 5° C.–15° C. overnight in a temperature gradient. After incubation, the ligation mixture was packaged into phage using an in vitro packaging extract (Gigapack® III Gold packaging extract; Stratagene Cloning Systems), and the resulting library was titered according to the manufacturer's specifications.

The human testis λZap® II library was used to infect *E. coli* host cells (XL1-Blue MRF' strain; Stratagene Cloning Systems), and $1.5 \times 10^6$ pfu were plated onto 150-mm NZY plates at a density of ~40,000 pfu/plate. The inoculated plates were incubated overnight at 37° C. Filter plaques lifts were made using nylon membranes (Hybond™-N; Amersham), according to the procedures provided by the manufacturer. The filters were processed by denaturation in solution containing 1.5 M NaCl and 0.5 M NaOH for 7 minutes at room temperature. The filters were blotted briefly on filter paper to remove excess denaturation solution, followed by neutralization for 5 minutes in 1 M Tris-HCl, pH 7.5, and 1.5 M NaCl. Phage DNA was fixed onto the filters with 1,200 µJoules of UV energy in a UV Crosslinker (Stratalinker®; Stratagene Cloning Systems). After fixing, the filters were prehybridized in hybridization solution (5× SSC, 5× Denhardt's solution, 0.2% SDS and 1 mM EDTA). Heat denatured, sheared salmon sperm DNA at a final concentration of 100 µg/ml was added. The filters were prehybridized at 65° C. overnight.

A probe was prepared as a PCR product by using oligonucleotide primers designed to amplify the human testis-specific insulin homolog cDNA coding corresponding to nucleotide 8 to nucleotide 568 of SEQ ID NO: 12. A PCR reaction mixture containing 2 µl of ZC10008 (SEQ ID NO: 4) and 2 µl of ZC10491 (SEQ ID NO: 5), 1 µl of 100 fentogram pSLHIT-10 (described in Example 5), 1 µl of 10 mM dNTPs, 10 µl of 10× KlenTaq buffer (Clontech), 82 µl water, and 2 µl KlenTaq DNA polymerase (Clontech). The PCR reaction was run as follows: 1 cycle at 94° C. for 1 minute; 30 cycles at 95° C. for 20 seconds, 60° C. for 20 seconds, 68° C. for 1 minute; and 1 cycle at 68° C. for 10 minutes. The PCR product was gel purified on a 1.5% low melt agarose gel.

Fifty nanograms PCR product was radiolabeled with $^{32}$Pα-dCTP by random priming using the MEGAPRIME™ DNA Labeling System (Amersham), according to the manufacturer's specifications. The prehybridization solution was replaced with fresh hybridization solution containing $1.4 \times 10^6$ cpm/ml labeled probe and allowed to hybridize for 64 hours at 60° C. After hybridization, the hybridization solution was removed and the filters were rinsed in a wash solution containing 0.25%× SSC, 0.25% SDS and 1 mM EDTA at 65° C. The filters were placed on autoradiograph film and exposed at −70° C. with intensifying screens for 96 hours.

Examination of the autoradiographs revealed 35 regions that hybridized with the labeled probe. Agar plugs were picked from 35 regions for purification. Each agar plug was soaked overnight in 1 ml of SM containing 1% (v/v) chloroform (Sambrook et al. *Molecular Cloning: A Laboratory Manual*, 2nd ed., Cold Spring Harbor Laboratory Press, Cold Spring Harbor, N.Y., 1989). After incubation, the phage from each plug were diluted 1:1000 in SM. Aliquots of 12.5 µl were plated on *E. coli* XL-1 Blue MRF' cells. The plates were incubated overnight at 37° C., and filter lifts were prepared, prehybridized, hybridized, washed and autoradiographed as described above. Examination of the resulting autoradiographs revealed positive signals on 3 filter lifts.

The plasmids were excised using an ExASSIST/SOLR™ system (Stratagene Cloning Systems), according to the manufacturer's specification. These plasmids were amplified by PCR for insert size determination and sequencing. A clone, designated pSLZpin2, was shown to be an insert of 717 bp and contained the sequence shown in SEQ ID NO: 12.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. An isolated, mature rat Zins2 testis-specific insulin homolog protein consisting of:

a B chain consisting of amino acid residue 22 to amino acid residue 52 of SEQ ID NO: 2;

an A chain consisting of amino acid residue 162 to amino acid residue 188 of SEQ ID NO: 2;

wherein the B chain and A chain are joined by inter- and intra-chain disulfide bonds.

2. An isolated, mature rat Zins2 testis-specific insulin homolog protein according to claim 1 consisting of:

a B chain consisting of the amino acid sequence from amino acid residue 23 to amino acid residue 51 of SEQ ID NO: 2;

an A chain consisting of the amino acid sequence from amino acid residue 163 to amino acid residue 188 of SEQ ID NO:2, wherein the B chain and A chain are joined by inter- and intra-chain disulfide bonds.

3. An isolated, mature human Zins2 testis-specific insulin homolog protein consisting of:

a B chain consisting of amino acid residue 20 to amino acid residue 54 of SEQ ID NO:13;

an A chain consisting of amino acid residue 172 to amino acid residue 213 of SEQ ID NO:13;

wherein the B chain and A chain are joined by inter- and intra-chain disulfide bonds.

4. An isolated, mature human Zins2 testis-specific insulin homolog protein according to claim 3 consisting of:

a B chain consisting of the amino acid sequence from amino acid residue 21 to amino acid residue 53 of SEQ ID NO:13;

an A chain consisting of the amino acid sequence from amino acid residue 173 to amino acid residue 198 of SEQ ID NO:13, wherein the B chain and A chain are joined by inter- and intra-chain disulfide bonds.

5. An isolated Zins2 testis-specific insulin homolog polypeptide selected from the group consisting of:

(a) polypeptides comprising a sequence of amino acids encoded by the nucleotide sequence as shown in SEQ ID NO: 1; and (b) allelic variants of (a).

6. A pharmaceutical composition comprising a polypeptide according to claim 5 in combination with a pharmaceutically acceptable vehicle.

7. An isolated Zins2 testis-specific insulin homolog polypeptide consisting of an amino acid sequence which is at least 85% identical to the amino acid sequence of SEQ ID NO:2.

8. An isolated Zins2 testis-specific insulin homolog polypeptide of claim 7, wherein any difference between said amino acid sequence of said isolated Zins2 testis-specific insulin homolog polypeptide and said corresponding amino acid sequence of SEQ ID NO:2 is due to a conservative amino acid substitution.

* * * * *